United States Patent
Lee et al.

(10) Patent No.: US 6,428,997 B1
(45) Date of Patent: Aug. 6, 2002

(54) **AMINOPEPTIDASE DERIVED FROM *BACILLUS LICHENIFORMIS* AND PROCESS FOR PREPARATION OF NATURAL TYPE PROTEINS**

(75) Inventors: Young-Phil Lee; Kyuboem Han; Se-Hoon Kim; Soon-Jae Park; Seung-Joo Lee, all of Taejon-si (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/367,940

(22) PCT Filed: Feb. 16, 1998

(86) PCT No.: PCT/KR98/00032
§ 371 (c)(1),
(2), (4) Date: Aug. 18, 1999

(87) PCT Pub. No.: WO98/38290
PCT Pub. Date: Sep. 3, 1998

(30) Foreign Application Priority Data

Feb. 28, 1997 (KR) ................................. 97-6756

(51) Int. Cl.[7] .......................... C12N 9/56; C12P 21/06; C07K 1/22
(52) U.S. Cl. ...................... 435/212; 435/68.1; 530/415
(58) Field of Search ................ 435/68.1, 212; 530/415

(56) References Cited

U.S. PATENT DOCUMENTS

| | | | |
|---|---|---|---|
| 4,865,974 A | * | 9/1989 | Ben-Bassat et al. ......... 435/68 |
| 4,870,017 A | * | 9/1989 | Ben-Bassat et al. ........ 435/212 |
| 5,013,662 A | * | 5/1991 | Ben-Bassat et al. ........ 435/212 |
| 5,753,465 A | * | 5/1998 | Ho et al. .................. 435/69.6 |
| 5,763,215 A | * | 6/1998 | Blumberg et al. .......... 435/69.1 |
| 6,071,718 A | * | 6/2000 | Mukerji et al. ............ 435/69.1 |

FOREIGN PATENT DOCUMENTS

| JP | 03-285684 A | * | 12/1991 |
|---|---|---|---|
| WO | WO-09/02813 A1 | * | 3/1990 |

OTHER PUBLICATIONS

Rodriguez–Absi, J., et al., "Isolation and proteties of an aminopeptidase from *Bacillus licheniformis*", Archives of Biochemistry and Biophyiscs, vol. 186, No. 2, pp. 383–391.*

Fujiwara, K. et al., "the substrate specificity of pyrrolidone carboxylyl peptidase from Bacillus amyloliquefaciens", Biocheimica et Biophysica Acta, vol. 570, pp. 140–148.*

An article entitled "Amino–Terminal Processing Of Proteins", By A. Ben–Bassat et al., Published by Nature vol. 326, pp. 315, Mar. 19, 1987.

An article entitled "Processing Of the Initiation Methionine From Proteins . . . ," By Basset et al., Published by Journal of Bacteriology, vol. 169, No. 2, pp. 751–757 Feb. 1987.

(List continued on next page.)

Primary Examiner—Ponnathapu Achutamurthy
Assistant Examiner—William W. Moore
(74) Attorney, Agent, or Firm—Bachman & LaPointe, P.C.

(57) ABSTRACT

The present invention relates to a process for removing methionine (Met) residue at N-terminus of proteins specifically. Particularly, the present invention relates to an aminopeptidase which is purified from *Bacillus licheniformis* removes a methionine residue from N-terminus of peptide and proteins. And the present invention relates to a process for preparing a natural type protein from proteins produced in microorganisms by recombinant DNA technology. Various kinds of natural type proteins such as human growth hormone (HGH) can be prepared massively and easily by the process of the present invention.

11 Claims, 12 Drawing Sheets

OTHER PUBLICATIONS

An article entitled "New Growth Industry in Human Growth Hormone", By Gina Kolata, Published Oct. 3, 1986 by in Science, vol. 34 pp. 22–24.

An article entitled "Clinical Studies With Recombinant–DNA–Derived . . . ", By Kaplan et al., published Mar. 29, 1986, by The Lancet, pp. 697–700.

An article entitled, "In–vivo Processing of the Initiator Methionine From Recombinant Methionyl . . . ", By Yasueda et al., published May 28, 1991, by Applied Microbiology and Biotechnology, vol. 36, pp. 211–215.

An article entitled "Enzymatic Cleavage of Amino Terminal Methionine From . . . ", By Nakagawa et al., Published 1987 by Bio/Technology, vol. 5, pp. 824–827.

An article entitled "High–Level Direct Expression Of Semi–Synthetic Human Interleukin–6 . . . ", By Yasueda et al., Published by Bio/Technology, vol. 8 Nov. 1990, pp. 1036–1040.

An article entitled, "Equivalent Potency and Pharmacokinetics of Recombinant . . . ", By Moore et al., published by Endocrinology, vol. 122, No. 6 pp. 2920–2926.

An article entitled "Bacterial Aminopeptidase: Properties and Functions", By Gonzales et al., published by FEMS Microbioloby Reviews, 18 pp. 319–344.

An article entitled "Isolation and Properties of an Aminopeptidase from *Bacillus lichenformis*", By Absi et al., published by Archives of Biochemistry and Biophysics, vol. 186, No. 2, Mar. 1978, pp. 383–391.

An article entitled, "*Bacillus Subtilis* Aminopeptidase: Purification, . . . " By Wagner et al., published by Archives of Biochemistry and Biophysics, vol. 197, No. 1, Oct. 1, 1979, pp. 63–72.

An article entitled "*Bacillus subtilis* Aminopeptidase: Specificity . . . ", By Ajabnoor et al., published by Archives of Biochemistry and Biophysics, vol. 202, No. 2, Jul. 1980, pp. 540–545.

An article published 1984. The article is in Russian and there is no English equivalent provided. (abstract).

* cited by examiner

AMINOPEPTIDASE DERIVED FROM *BACILLUS LICHENIFORMIS* AND PROCESS FOR PREPARATION OF NATURAL TYPE PROTEINS

The instant application is a continuation of International Application No. PCT/KR98/00032, filed Feb. 16, 1998 the benefit of which is claimed herein under 35 U.S.C. 371.

FIELD OF THE INVENTION

The present invention relates to a process for removing a methionine (Met) residue at the N-terminus of peptides and proteins specifically.

Particularly the present invention relates to aminopeptidases which are derived from *Bacillus licheniformis* removes a methionine residue from the N-terminus of peptides and proteins. And the present invention relates to a process for preparing a natural type protein from recombinant proteins produced in microorganism. Various kinds of natural type proteins such as human growth hormone (HGH) can be prepared massively and easily by the process of the present invention.

BACKGROUND OF INVENTION

Recombinant DNA technology permits large scale production of eukaryotic proteins in bacteria. However the proteins so produced are frequently characterized by the addition of an extra methionine residue at their N-terminus. The proteins containing the N-terminal methionine may induce immunogenic reaction in human and animal bodies and may not express effectively their original function. Therefore the process for preparing natural type proteins should be developed (Nature, 326, 315, 1987; J. Bacteriol., 169, 751–757, 1987; Bio/Technology, 8, 1036–1040, 1990; Appl. Microbiol. Biotechnol., 36, 211–215, 1991) to overcome the problems.

Especially human growth hormone (HGH) is a polypeptide composed of 191 amino acids, having 22, 125 kDa of molecular weight and containing Phe-Pro-Thr sequence at the N-terminus. And HGH is produced in human pituitary gland and used mostly to improve dwarfism (Raben, M. S., J. Clin. Endocr., 18, 901, 1958). Initially HGH has been extracted and purified from human pituitary gland to be utilized for medicinal treatment. However HGH has not been provided sufficiently to satisfy all the patients since the above process limits the HGH amount produced. And it is also reported that 4 children inoculated with HGH purified from hypothalamus have been infected with virus and died. Thus FDA has prohibited administration of HGH produced by the process for the treatment of patients (Science, 234, 22, 1986). Recently many researchers have attempted to produce HGH in *Escherichia coli* or yeast by using recombinant DNA technology and to utilize this HGH clinically (in *E. coli*, Korean Patent Publication No. 89-1244 and No. 87-701, Patent Laid-open No. 87-2258 and No. 84-8695; in yeast, Patent Publication No. 92-99 and Patent Laid-open No. 90-9973 and No. 90-9976).

Generally recombinant HGH has an extra methionine residue which is added at the N-terminus during protein synthesis by initiation codon although natural type HGH is composed of 191 amino acids without the methionine. Thus the recombinant HGH is produced as a form of methionyl HGH which is composed of 192 amino acids and contains Met-Phe-Pro-Thr sequence at the N-terminus. In respect of biological activity, methionyl HGH exhibits the same activity with that of natural type HGH (Moore, J. A., Endocrinology, 122, 2920–2926, 1988). Any other side-effect which an extra methionine induces has not been reported. But it is reported that antibodies against an extra methionine may be generated, of which the rate is higher than that of natural type proteins (Lancet, Mar. 29, 697, 1986).

Therefore, many researchers have attempted to produce natural type HGH without the N-terminal methionine. In particular a method has been developed to obtain natural type HGH in culture broth, which comprises fusing the N-terminus of HGH to a C-terminus of other proteins and cutting the fusion protein with specific protease (PCT WO 89/12678; EP 20209; EP 321940). And a method also has been attempted, which comprises expressing HGH in cell cytoplasm, secreting it out of cell an removing a methionine residue during secretion (EP 008832; U.S. Pat. No. 4,755, 465; JP 01273591; EP 306673; Korean Patent Appl. No. 92-10932). Unfortunately these methods have some difficulties to perform complicated manipulation such as preparing expression vectors and transforming host cells. In addition fermentation condition should be optimized in each case.

And a method has been exploited in case of recombinant proteins containing an extra amino acid at the N-terminus, which uses aminopeptidases to remove the N-terminal amino acid and prepares natural type proteins by simple process. For example natural type HGH can be prepared from methionyl HGH when specific aminopeptidase removing the N-terminal methionine selectively is used. At that time methionyl HGH can be prepared in mass by the process already established (PCT WO 86/04609; WO 86/204527 A1).

Hitherto, several aminopeptidases which can be used to prepare natural type HGH have been reported, such as aminopeptidase purified from *Aeromonas proteolytica* (PCT WO 86/01229; EP 0489711 A3, B.T.G. Co.; Prescott and Wikes, Method in Enzymology, 44, 530–543, 1976), aminopeptidase from pig kidney (PCT 86.204527 A1; Bio/Technology, 5, 824–827, 1987, Takeda Co.), dipeptidyl aminopeptidase from *Dictyostelium discoidem* (EP 557076 A1; U.S. Pat. No. 5,126,249, Eli Lilly Co.) and aminopeptidase from *Streptomyces thermonitrificans* (EP 6296695; U.S. Pat. No. 5,569,598; Lucky Co.).

However the aminopeptidase should react with only extra amino acid residues of proteins at the N-terminus, not with naturally occurring sequences of amino acids in order to prepare natural type proteins. That is, when N-terminal amino acid sequences are X-Y-Z in natural type protein and Met-X-Y-Z in recombinant protein respectively, aminopeptidase which removes the methionine residue without reacting other amino acids, such as X-Y-Z-, is preferred to prepare the same protein with natural type proteins. Thus substrate specificity of aminopeptidase is important to satisfy the above conditions. Since methionyl HGH has Met-Phe-Pro-Thr-Ile amino acid sequence at the N-terminus, aminopeptidase for the use should recognize X-Pro sequence and stop cutting reaction in front of X amino acid to remove the N-terminal methionine selectively. For industrial use the enzyme also exhibits higher specific activity outstandingly.

Various kinds of aminopeptidase have been purified from microorganisms. Most of aminopeptidases require $Ca^{2-}$, $Zn^{2-}$ or other metal ions for their activities and remove amino acid residues at the N-terminus commonly. But aminopeptidases purified from different microorganisms have different enzymatic properties in respect of molecular weight, requirements of metal ions, optimal condition of reaction and substrate specificity (*FEMS Microbiol. Rev.*, 18, 319–344, 1996). These aminopeptidases are classified into exo-peptidase removing amino acid from the N-terminus of substrate proteins gradually.

Presently aminopeptidases which have been purified from Bacillus genus are from *Bacillus subtilis* (*Arch. Biochem. Biophys.*, 197, 63–77, 1979; *Arch. Biochem. Biophys.*, 202, 540–545, 1980; *J. Biochem.*, 107, 603–607, 1994; JP 03285684, Diacel-Chem Co.), *Bacillus stearothermophilus* (*Meth. Enzymol.*, 19, 544–552, 1970; *Biochem. Biophys. Acta*, 438, 212–220, 1976; EP 101653, Unitika), *Bacillus thuringensis* (Biokhimiya, 49, 1899–1907, 1984), *Bacillus licheniformis* (*Arch. Biochem. Biophys.*, 186, 383–391, 1978; *Microbiol.* Zh., 51, 49–52, 1989) and so forth.

In references cited above, aminopeptidases were analyzed to examine their enzymatic properties by using several substrates such as leucine-p-nitroanilide, dipeptide and the like. But oligopeptide and protein containing Met-X-Pro sequence at the N-terminus have not been used to examine aminopeptidases activity. Thus it has not been expected that aminopeptidases can be used for removal of only an extra methionine from recombinant proteins containing Met-X-Pro sequence at the N-terminus.

In order to prepare natural type proteins by using recombinant DNA technology, we have investigated and purified aminopeptidases of *Bacillus licheniformis* strains which remove only a methionine residue at the N-terminus of proteins. Aminopeptidases derived from *Bacillus licheniformis* an remove a methionine residue from synthetic substrate, oligopeptide, protein and so on properly and recognize Met-X-Pro sequence (X indicates any amino acid available) specifically. Thus we have demonstrated that aminopeptidases of the present invention can be used to prepare natural type HGH efficiently.

SUMMARY OF THE INVENTION

The object of the present invention is to provide aminopeptidases derived from *Bacillus licheniformis* which removes a methionine residue at the N-terminus of peptide and protein.

The aminopeptidases of the present invention recognize Met-X-Pro sequence at the N-terminus of peptide and protein to remove the methionine residue. Preferably X is phenylalanine.

The aminopeptidases contain amino acid sequences of SEQ ID. NO: 3 (Lys-Phe-Ser-Lys-Lys-Phe-Asn-Glu-Asn-Arg sequence), and SEQ ID. NO: 4 (Lys-Phe-Ser-Lys-Phe-Asn-Glu-Asn-Arg-Ala-Tyr-Gln-Tyr-Ile-Tyr-His-Leu sequence), at the N-terminus or sequence which are deleted and substituted in amino acids from the N-terminus of the above sequences.

The aminopeptidases have a molecular weight at the range of 43–47 kDa on SDS-PAGE.

The aminopeptidases are active at the range of pH 7.5–10.5 preferably and more preferably at the range of pH 8.5–9.5.

The aminopeptidases are active at the range of 40–70° C. preferably and more preferably at the range of 50–60° C.

The aminopeptidases are thermostable and maintains 50% activity even though it is incubated at 60° C. for 4 hours.

The aminopeptidases activity are inhibited by dithiothreitol, iodoacetic acid and ortho-penanthroline and inhibited partially by ethylenediaminetetraacetic acid (EDTA).

Another object of the present invention is to provide processes for preparation of the aminopeptidases, Which comprise culturing *Bacillus licheniformis*, centrifuging the culture broth to obtain supernatant and performing gel filtration chromatography with the concentrated supernatant. Preferably *Bacillus licheniformis* strain is KCTC 3058, KCTC 12759, KCTC 3045 and KCTC 1030 in the above description.

The present invention provides a process for preparation of the aminopeptidases, which comprises preparing aminopeptidase-producing cells by using recombinant DNA technology, culturing the recombinant cells and purifying the enzyme.

Another object of the present invention is to provide a process for preparing natural type proteins, which uses recombinant proteins produced by using recombinant DNA technology with aminopeptidase and purifying proteins.

Precisely the present invention provides a process for preparing natural type HGH from methionyl HGH containing Met-X-Pro sequence at the N-terminus.

The process for preparation comprises using aminopeptidase at the range of pH 7.0–9.5 and at the range of 20–60° C. and purifying natural type HGH through ion exchange resin chromatography and so forth. At that time NaCl is added to 30–230 mM into reaction mixture and enzymes is added at the range of 0.2–20 U per 1 mg of methionyl HGH preferably.

Practical and presently preferred embodiments of the invention are illustrative as shown in the following examples.

However, it will be appreciated that those skilled in the art, on consideration of this disclosure, may make modifications and improvements within the spirit and scope of the present invention.

DETAILED DESCRIPTION OF THE INVENTION

Aminopeptidases of this invention, which removes a methionine residue at the N terminus of peptides and proteins, is derived from *Bacillus licheniformis*. Approximately 20 strains of *Bacillus licheniformis* deposited in Korean Collection for Type Culture (KCTC) are examined and their aminopeptidase activities existing in culture broth are compared respectively.

Considering references reported previously, *Bacillus licheniformis* strains are divided as alkaline protease (containing detergent-resistant alkaline protease) producing strain, α-amylase producing strain and bacitracin-producing strain.

Figure 1:
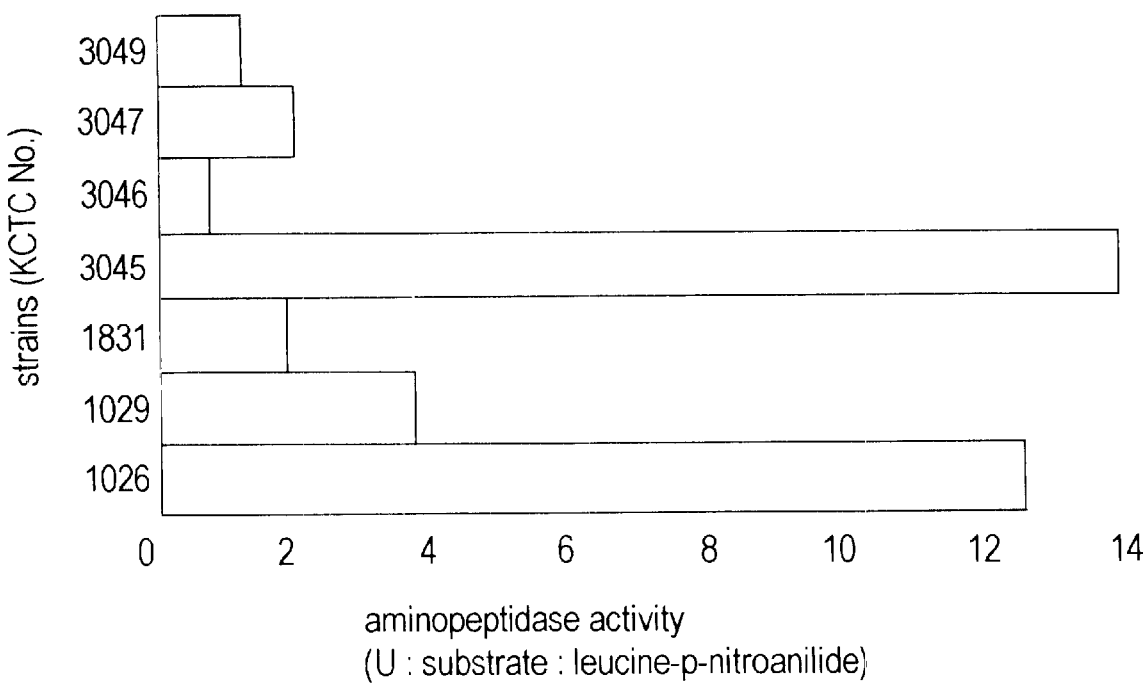
FIG. 1 shows the quantity of aminopeptidase which is produced from culture broth of alkaline protease producing *Bacillus licheniformis* strains such as KCTC 1026, KCTC 1029, KCTC 1831, KCTC 3045, KCTC 3046, KCTC 3047, and KCTC 3049. As substrate, leucine-p-nitroanilide is used to measure the enzyme activity.

In detail 7 alkaline protease-producing strains of *Bacillus licheniformis* such as KCTC 1026 (ATCC 21415), KCTC 1029 (ATCC 21418), KCTC 1831 (ATCC 21424), KCTC 3045 (ATCC 21415), KCTC 3046 (ATCC 21416), KCTC 3047 (ATCC 21417), KCTC 3049 (ATCC 21424) (see FIG. 1), 3 α-amylase-producing strains KCTC 1030 (ATCC 27811), KCTC 2215 (ATCC 27811), KCTC 3006 (ATCC 39326) (see FIG. 2), and 3 bacitracin-producing strains such as KCTC 3056 (ATCC 10716, ATCC 11944), KCTC 3057 (ATCC 11945), KCTC 3058 (ATCC 11946) (see FIG. 3) are cultured. And in the supernatant of culture broth aminopeptidase activities are measured by the process described in Reference Example 1.

Figure 4:
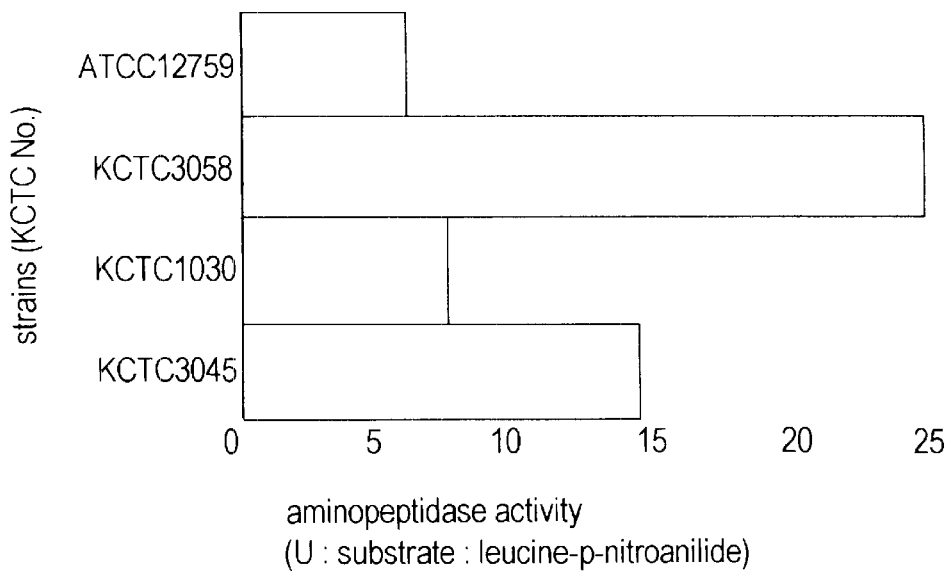
FIG. 4 shows the aminopeptidase activity of *Bacillus licheniformis* ATCC 12759 to compare with that of *Bacillus licheniformis* KCTC 3045, KCTC 1030 and KCTC 3058 having higher aminopeptidase activity. As substrate, leucine-p-nitroanilide is used to measure the enzyme activity.

As a result, 6–25 U range of aminopeptidase activities is observed in *Bacillus licheniformis* KCTC 3045, KCTC 1030, KCTC 3058 and ATCC 12759 strains by using leucine-p-nitroanilide as substrate (see FIG. 4). Among these *Bacillus licheniformis* strains ATCC 12759 strain, has been already reported by Rodriquez et. al., to produce an aminopeptidase (Rodriguez-Absi, J. and Prescott, J. M., *Arch. Biochem. Biophys.*, 186(2), 383–391, 1978).

Reference Example 1

Measurement of Aminopeptidase Activity by Using Leucine-p-nitroanilide as Substrate Aminopeptidase activities of this invention were measured by the method of Pfleiderer (Pfleiderer, *Meth. Enzymol.*, 19, 514–521, 1970). Precisely, 1 U of enzyme activity defines the enzyme quantity changing 1 absorbance at 405 nm which is measured by the process adding aminopeptidase in 1 ml solution of 100M Tris-Cl (pH 8.0) and 2 mM leucine-p-nitroanilide (Sigma, USA), incubating at 37° C. for 1 min, then adding 100 μl of 70% acetic acid to stop the reaction. At that time leucine-p-nitroanilide was dissolved in dimethylsulfoxide (DMSO) to make 100 mM solution.

Figure 5:
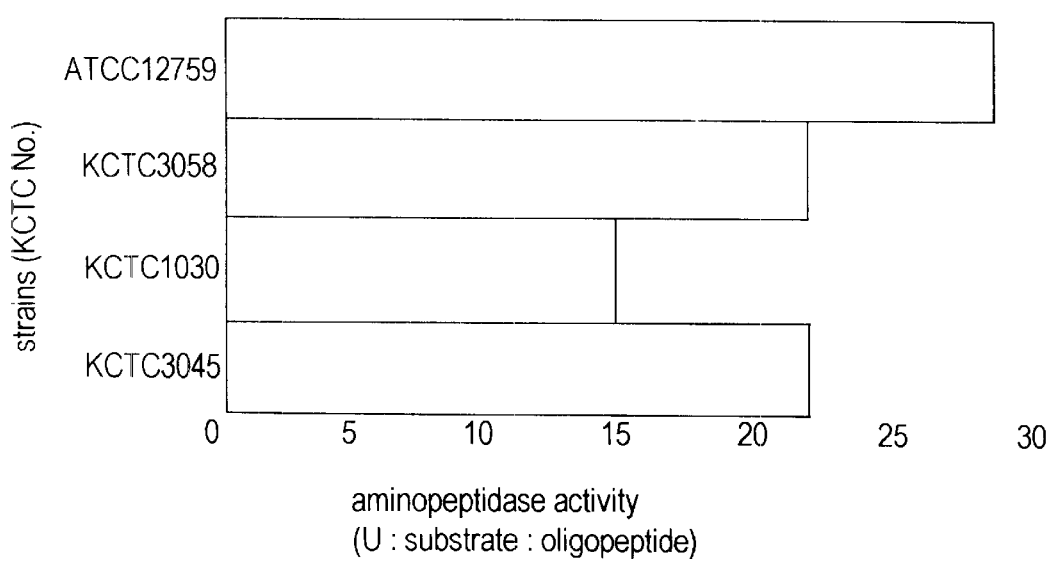
FIG. 5 shows aminopeptidase activity of *Bacillus licheniformis* ATCC 12759 to compare with that of *Bacillus licheniformis* KCTC 3045, KCTC 1030 and KCTC 3058 having higher aminopeptidase activity. As substrate, oligopeptide containing Met-Phe-Pro-X sequence, the N-terminal sequence of HGH, is used to measure the enzyme activity.

And the aminopeptidase activities of *Bacillus licheniformis* strains described above are also measured by using methionyl oligopeptide as substrate in order to detect exopeptidase activity removing methionine residues of peptides and proteins containing N-terminal methionine (see FIG. 5). Precisely oligopeptide containing amino acid sequence of SEQ ID.NO: 1 (Met-Phe-Pro-Thr-Giu-Pro-Ser) is used as substrate to measure aminopeptidase activity by the process described in Reference Example 2.

Reference Example 2

Measurement of Aminopeptidase Activity by Using Oligopeptide as Substrate

In order to measure aminopeptidase activities, reaction mixture containing substrate and aminopeptidase with known concentrations in buffer solution of 0.1M Tris.Cl, 0.1M NaCl was prepared. As substrate oligopeptide having amino acid sequence of SEQ ID.NO: 1 was used. The reaction proceeded at 37° C. for predetermined time and equal volume of 70% acetic acid was added to stop it. Then high performance liquid chromatography (HPLC) was performed to analyze the reaction product. Oligopeptide was dissolved in DMSO to make 30 mM solution, diluted in 2.5 mM by using DW and added into above reaction mixture with proper concentration.

Chromatography was performed to analyze the reaction product in the reaction condition as follows. Precisely YMC protein RP column (4.6*250 mm, YMC Co.), solvent A containing 0.05% trifluoroacetic acid (TFA) and solvent B containing 0.05% trifluoroacetic acid and 80% acetonitrile were utilized for elution. The above mixture was injected into column and eluted with solvent B having linear concentration gradient of 10%–30%. Then area which is recording absorbance at 214 nm was calculated. As a result substrate which was not reacted was eluted at about 9.5 min and reaction product at about 7.0 min in above reaction condition. Eluting substrate and reaction product peptide in such condition, area of each peak was proportionate to number of amino acids of peptide. Thus the proportion of area in substrate (6 peptide bonds) and product (5 peptide bonds) of the same concentration was 6:5 approximately. Therefore the concentration of product peptide produced in the above reaction was obtained by the formula as shown below.

[P]=(PA/5)/(SA/6+PA/5)*[S]
PA: peak area of product peptide
SA: peak area of substrate peptide
[S]: initial concentration of substrate peptide
[P]: concentration of product peptide produced by the process Since oligopeptide mentioned above contains a N-terminal methionine and adjacent X-Pro sequence, aminopeptidase which reacts only with the N-terminus, not with X-Pro sequence can be selected easily by using the oligopeptide. Precisely, *Bacillus licheniformis* strains such as KCTC 3045, KCTC 1030, KCTC 3058 and ATCC 12759 are assayed to produce aminopeptidase having properties mentioned above. Thus these aminopeptidase derived from these strains can be adopted usefully to remove the N-terminal methionine from peptides and proteins containing Met-X-Pro sequence at the N-terminus.

In addition, the aminopeptidase activity is also examined in order to identify the removal of N-terminal methionine from protein having higher molecular weight. At that time, aminopeptidase has been purified highly in order to diminish the additional reaction prompted by other endoproteases.

Precisely aminopeptidases of *Bacillus licheniformis* ATCC 12759 and KCTC 3058 are purified and their enzymatic properies are examined. The aminopeptidase indicates the highest reactivity with oligopeptide referring to the reactivity with leucine-p-nitroanilide.

Figure 6:
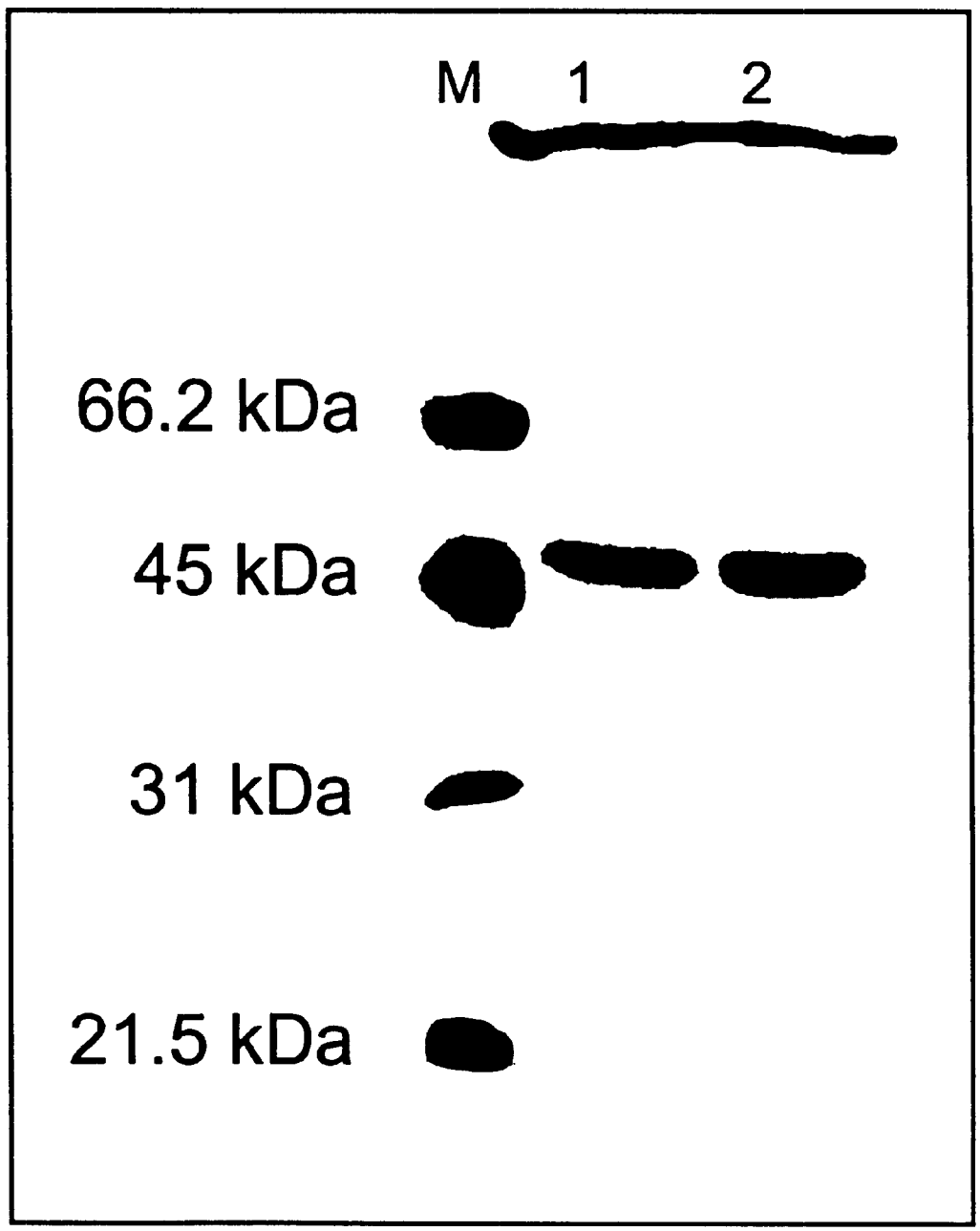
FIG. 6 shows purity and molecular weight of aminopeptidase purified from *Bacillus licheniformis* ATCC 12759 strain, which is depicted by SDS-PAGE.

The aminopeptidases of the present invention is analyzed by SDS-polyacrylamide gel electrophoresis (SDS-PAGE) and have a molecular weight at the range of 43–47 kDa (see FIG. 6 and FIG. 16).

And it is identified that the aminopeptidase have the amino acid sequence of SEQ ID. NO: 3 (Lys-Phe-Ser-Lys-Lys-Phe-Asn-Glu-Asn-Arg) and SEQ ID. NO: 4 (Lys-Phe-Ser-Lys-Lys-Phe-Asn-Glu-Asn-Arg-Ala-Tyr-Gln-Thr-Ile-Tyr-His-Leu sequence) at the N-termini.

The aminopeptidase purified from *Bacillus licheniformis* ATCC 12759 coexists with deleted forms of enzyme without 1 or 2 amino acids at the N-terminus and the aminopeptidase purified from *Bacillus licheniformis* KCTC 3058 coexists with lysine-deleted form or with substituted form at the 9th amino acid (from asparagine to aspartic acid).

Generally, the aminopeptidases of the present invention can be classified into leucine aminopeptidase since it has specific and higher reactivity in leucine than that in methionine.

Detaily the enzymatic properties of aminopeptidases are examined by using leucine-p-nitroanilide as synthetic substrate. The aminopeptidases of this invention are preferably active at the range of pH7.5–10.5 and more preferably at the range of pH8.5–9.5 (see FIG. 7).

Figure 8:
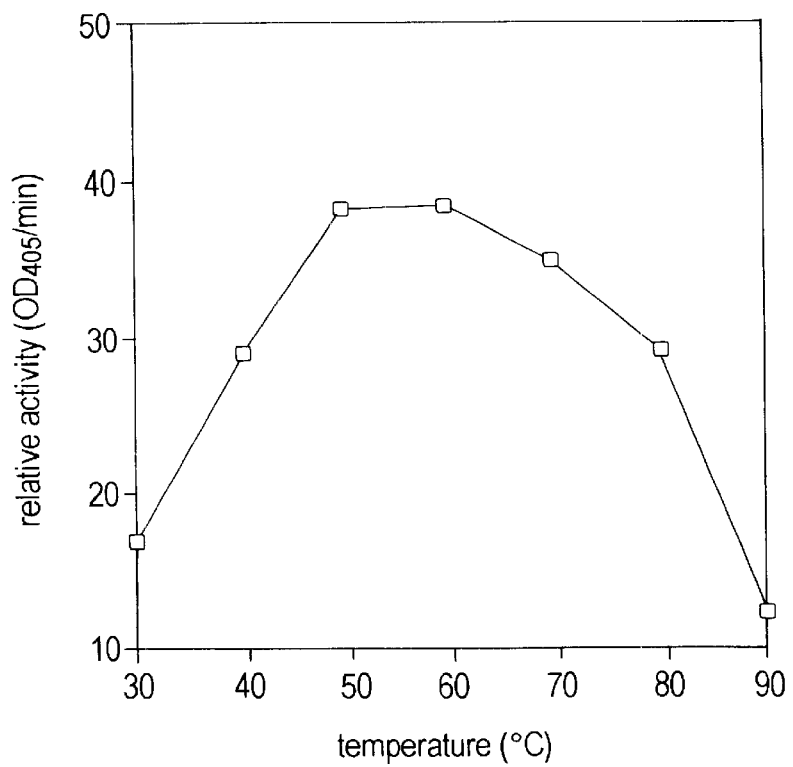
FIG. 8 shows aminopeptidase activities according to temperature variation, which are measured by using leucine-p-nitroanilide as substrate.

And the aminoepetidases are preferably active at the range of 40–70° C. and more preferably at the range of 50–60° C. (see FIG. 8). And aminopeptidases are thermostable and maintain more than 50% activity even though it is incubated at 60° C. for 4 hours (see FIG. 9). The aminopeptidase activities are inhibited by dithiotreitol, iodoacetic acid, ortho-penanthroline and inhibited partially by ethylene diamine tetraacetic acid(EDTA).

The present invention provides processes for preparing aminopeptidases derived from *Bacillus licheniformis*.

Precisely in order to prepare the aminopeptidase, culture broth of *Bacillus licheniformis* strain is obtained, centrifuged and then supernatant of the culture broth is concentrated to perform gel permeation chromatography and so forth. At that time, *Bacillus licheniformis* ATCC 12759, KCTC 3058, KCTC 3045 and KCTC 1030 strains can be used preferably.

In addition, amionpeptidase producing cells is prepared by using recombinant DNA technology, cultured and then the aminopeptidase can be purified.

The present invention provides a process for preparing natural type proteins from recombinant proteins.

In addition, the process of the present invention for preparing natural type proteins comprises treating proteins produced by recombinant DNA technology with the aminopeptidase and purifying products which is exactly same with naturally occurring protein.

Precisely natural type HGH in which methionine is free at the N-terminus is prepared from methionyl HGH containing Met-X-Pro sequence and so forth by the process described above. At that time 0.2–20 U of aminopeptidase per 1 mg of 1 mg methionyl HGH is treated, preferably at the range of pH 7.0–9.5 (see FIG. 10), at the range of 20–60° C., more preferably 37° C. (see FIG. 11). And NaCl is added to 30–230 mM preferably, 100 mM more preferably (see FIG. 12). And ion exchange resin chromatography is performed after treating aminopeptidase to purify natural type HGH obtained by the process mentioned above (see FIG. 13).

EXAMPLES

Example 1

Activity Measurement of Aminopeptidase from Alkaline Protease-producing *Bacillus licheniformis*

7 *Bacillus licheniformis* strains, KCTC 1026 (ATCC 21415), KCTC 1029 (ATCC 21418), KCTC 1831 (ATCC 21424), KCTC 3045 (ATCC 21415), KCTC 3046 (ATCC 21416), KCTC 3047 (ATCC 21417) and KCTC 3049 (ATCC 21424), which have been known to produce alkaline protease were inoculated into 100 ml of broth containing ampicillin in autoclaved 500 ml flask (AP-broth) and incubated at 30° C. for more than 50 hours with shaker of 150 rpm.

1 ml of culture broth obtained above was centrifuged and in the supernatant aminopeptidase activity was measured by using leucine-p-nitroanilide as substrate. The result were shown in FIG. 1. In most strains of *Bacillus licheniformis* aminopeptidase activities were assayed and the exact values were 12.3 U, 3.62 U, 1.87 U, 13.6 U, 0.67 U, 1.98 U and 1.25 U respectively.

Example 2

Activity Measurement of Aminopeptidase from -amylase-producing *Bacillus licheniformis*

Figure 2:
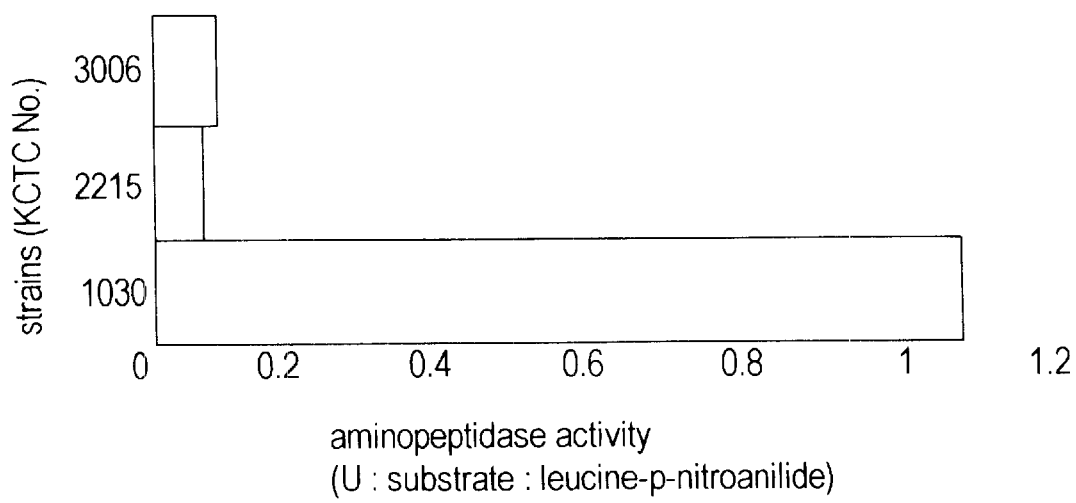
FIG. 2 shows the quantity of aminopeptidase which is produced from culture broth of α-amylase- producing *Bacillus licheniformis* strains such as KCTC 1030, KCTC 2215 and KCTC 3006. As substrate, leucine-p-nitroanilide is used to measure the enzyme activity.
Figure 3:
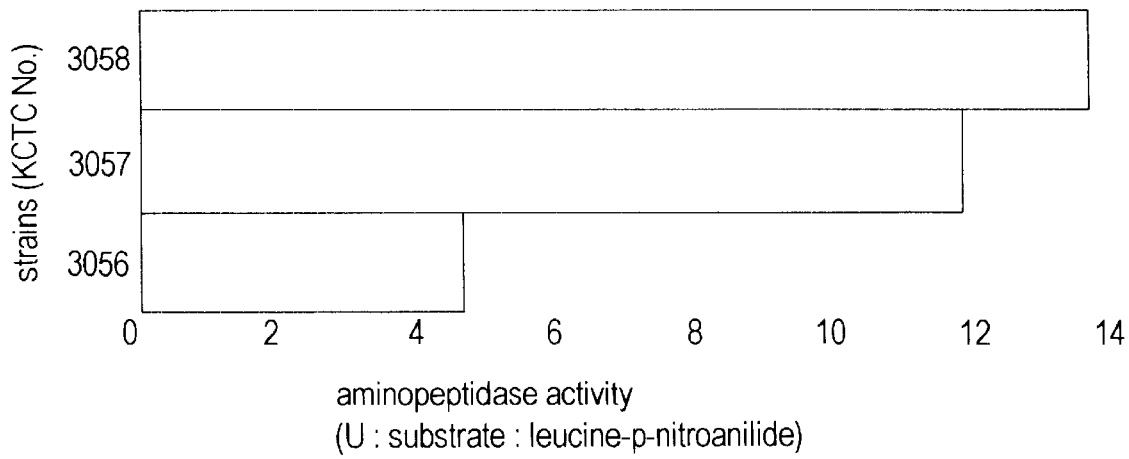
FIG. 3 shows the quantity of aminopeptidase which is produced from culture broth of bacitracin producing *Bacillus licheniformis* strains such as KCTC 3056, KCTC 3057 and KCTC 3058. As substrate, leucine-p-nitroanilide is used to measure the enzyme activity.

3 *Bacillus licheniformis* strains, KCTC 1030 (ATCC 27811), KCTC 2215 (ATCC 27811) and KCTC 3006 (ATCC 39326), which have been known to produce α-amylase, were incubated in flask (AP broth) by the same method of Example 1. Then the supernatant of culture broth was obtained, in which aminopeptidase activity was measured by using leucine-p-nitroanilide as substrate. The result were shown in FIG. 2. As shown in FIG. 2 aminopeptidase activities were assayed and the exact values were 1.04 U, 0.08 U and 0.09 U respectively. These enzymes activities measured by using leucine-p-nitroanilide were much lower than that of other *Bacillus licheniformis* strains.

Example 3

Activity Measurement of Aminopeptidase from Bacitracin-producing *Bacillus licheniformis*

3 *Bacillus licheniformis* strains, KCTC 3056 (ATCC 10716, ATCC 11944), KCTC 3057 (ATCC 11945) and KCTC 3058 (ATCC 11946), which have been known to produce bacitracin, were incubated in flask (AP broth) by the same method of Example 1. Then the supernatant of culture broth was obtained, in which aminopeptidase activity was measured by using leucine-p-nitroanilide as substrate. The results were shown in FIG. 3. The exact values of aminpeptidase activities were calculated as 4.40 U, 11.8 U and 13.3 U respectively.

Example 4

Activity Measurement of Aminopeptidase from Aminopeptidase Producing *Bacillus licheniformis* ATCC 12759

*Bacillus licheniformis* ATCC 12759 which has been known to produce aminopeptidase was incubated in flask by the same method of Example 1. Then the supernatant of culture broth was obtained, in which aminopeptidase activity was measured by using leucine-p-nitroanilide as substrate. The result were shown in FIG. 4. The exact values of aminopeptidase activities were 4.16 U which was intermediate comparing with that of other *Bacillus licheniformis* strains.

Example 5

Activity Measurement of Aminopeptidase in Large-scale Culture Broth by Using Leucine-p-nitroanilide as Substrate With reference to the results of Example 1, 2 and 3, *Bacillus licheniformis* strains which have high aminopeptidase activities such as KCTC 3045 (ATCC 21415), KCTC 1030 (ATCC 27811) and KCTC 3058 (ATCC 11946) were selected. These 3 *Bacillus licheniformis* strains and *Bacillus licheniformis* ATCC 12759 were inoculated into 50 ml of LB broth (yeast extract 5 g/l, bacto-tryptone 10 g/l, NaCl 5 g/l) in autoclaved 50 ml flask and incubated at 30° C. for 20 hours with shaker of 150 rpm. Then the culture broth was inoculated into 5 L of AP broth (glucose 10 g/l, potassium phosphate mono-basic 10 g/l, di-basic 10 g/l, NaCl 5 g/l, yeast extract 5 g/l, bacto-peptone 10 g/l, magnesium sulfate 0.01 g/l, $FeSO_4 \cdot 7H_2O$ 1 mg/l, $ZnSO_4 \cdot 7H_2O$ 1 mg/l, $MnSO_4 \cdot H_2O$ 1 mg/l) in autoclaved 5 L fermented and incubated at 37.5° C. for more than 50 hours with shaker of 300–400 rpm. 1 ml of culture broth were obtained and centrifuged.

Then in the supernatant aminopeptidase activities were measured by using leucine-p-nitroanilide as substrate. The results were shown in FIG. 4. In each *Bacillus licheniformis* strain aminopeptidase activities were assayed and the exact values were 14.6 U, 7.86 U 24.4 U and 6.10 U respectively. Among these strains *Bacillus licheniformis* ATCC 12759 has lowest aminopeptidase activity and *Bacillus lichenifor-mis* KCTC 3058 has 4 times higher activity than that of ATCC 12759 strain.

Example 6

Activity Measurement of Aminopeptidase in Large-scale Culture Broth by Using Oligopeptide as Substrate Aminopeptidase activity was measured by the process using culture broth obtained in Example 5 and oligopeptide as described below. Into reaction buffer (0.1M Tris-Cl, pH 8.0, 0.1M NaCl, 1.25 mM methionyl oligopeptide of SEQ ID. NO: 1 (Met-Phe-Pro-Thr-Glu-Pro-Ser sequence)) culture broth having 0.2 U of enzyme activity in leucine-p-nitroanilide substrate was added, adjusted to 0.3 ml of final volume and incubated at 37° C. for 10 min. Then 0.3 ml of 70% acetic acid was added to stop the reaction. Contaminant was removed by centrifuging at 14,000 rpm, for 5 min and filtering with 4 μm membrane sequentially. The reaction mixture was analyzed by HPLC and aminopeptidase activity in oligopeptide substrate was measured by the method of Reference Example 2.

The aminopeptidase activity were examined in *Bacillus licheniformis* KCTC 1030 (ATCC 27811), KCTC 3058 (ATCC 11946), ATCC 12759 and the exact values were 2.11, 1.46, 2.14 and 2.76μ mole/min respectively. Since these aminopeptidase removed only methionine residue of oligopeptide at the N-terminus without proceeding reaction, it can be used to remove a methionine residue in both oligopeptide and protein containing Met-X-pro sequence at the N-terminus. Since the enzyme activity measured by using oligopeptide and leucine-p-nitroanilide has some difference in spite of the same unit of culture broth, the enzyme activities may have no relation in two substrates as described.

As a result, it is proved that the aminopeptidase derived from *Bacillus licheniformis* can be used properly to remove a methionine residue at the N-terminus by using methionyl oligopeptide as substrate. In respect of substrate specificity, aminopeptidase did not react with X-pro sequence of the N-terminus although it can remove a methionine residue of the N-terminus.

It is also identified that the aminopeptidase derived from *Bacillus licheniformis* can be used properly to remove a methionine residue by using protein substrate as described in Examples below. As protein substrate methionyl HGH containing Met-X-Pro sequence at the N-terminus (initiated with Met-Phe-Pro-Thr-Ile sequence at N-terminus) was attempted for the use. When protein was utilized as substrate, contaminating proteases such as endo-proteases induced additional reactions. Thus aminopeptidase produced in *Bacillus licheniformis* strains should be purified highly before the reaction.

As shown in FIG. 5, the aminopeptidase purified from *Bacillus licheniformis* ATCC 12759, KCTC 3058 and so forth has the highest aminopeptidase activity in oligopeptide substrate which is compared with that of *Bacillus licheniformis* strains of the present invention. At that time the aminopeptidase activity in leucine-p-nitroanilide was used as standard. Therefore aminopeptidase purified in mass was adopted usefully in the process removing a methionine residue from methionyl HGH.

Example 7

Cultivation of *Bacillus licheniformis* ATCC 12759

In order to obtain *Bacillus licheniformis* ATCC 12759 in mass, *Bacillus licheniformis* strains were inoculated into 100 ml of autoclaved LB broth and incubated at 37° C. for 20 hours for seed culture. The culture broth was inoculated into 10 L of autoclaved LB broth in fermenter of 10 L volume and incubated for 22–24 hours maintaining pH 7.0.

Example 8

Purification of Aminopeptidase from *Bacillus licheniformis* KCTC 12759

Culture broth obtained in Example 7 (approximately 9 L) was centrifuged at 8000 rpm for 20 min. The resulting supernatant was exploited, added 1 mM PMSF (Phenylmethylsulfonylfluoride) and concentrated into about 1.5 L by using concentrator (Amicon Spiral Cartridge, MWCO 10000). Into above concentrating solution acetic acid was added to control pH 5.0 and ammonium sulfate was added to make 40% of final concentration (weight/volume). And the same volume of ter-butanol was added, mixed for 1 hour, then centrifuged to recover lower aqueous layer by using separating funnel (1st TTP). Then pH was adjusted to 6.0 by adding 0.5N NaOH and ammonium sulfate was also added to make 85% solution of final concentration. Then the same volume of ter-butanol was added, mixed for 1 hour, then centrifuged for 10 min to recover protein precipitation layer in middle band (2nd TTP).

Precipitated protein was dissolved in 20 mM PBS (pH 6.8) and centrifuged at 10,000 rpm for 20 min to remove contaminating precipitate. Considering conductivity of the solution, salt concentration was adjusted below 0.3M approximately. Then 1.5 L of SP-Sepharose (Pharmacia) was filled into INdeX 220/500 and equilibrated with same buffer. The above protein sample was injected, then the column was washed with PBS buffer containing 0.3–0.4M NaCl (flow rate 50 ml/min). Aminopeptidase was eluted with linear concentration gradient of 0.3–0.4M NaCl to 1M NaCl (flow rate 25 ml/min).

Each fraction eluted from SP-Sepharose column was examined to measure enzyme activity of aminopeptidase. And fractions indicating the enzyme activity were collected and concentrated into 20 ml by ultrafiltration (Amicon stirred cell type). Then gel filtration chromatography was performed by using packed column of 1800 ml Sephacryl S-200 and 20 mM PBS buffer (pH 6.8) containing additional 0.25M NaCl was used for elution.

Above fractions obtained by using gel filtration chromatography was concentrated and diluted with 20 mM phosphate buffer (pH 6.8). Then the diluted sample was adsorbed into FPLC mono-S column (0.5 cm*5 cm) equilibrated 3 times with the buffer and proteins were eluted with linear gradient of 0.3 to 1M NaCl for obtaining pure aminopeptidase. Although aminopeptidase eluted had several peaks on the column chromatography, all the peaks had same molecular weights measured by SDS-PAGE as shown in FIG. 6. In addition all the peaks indicated also same enzyme activities. And it was proved by N-terminal sequencing of the aminopeptidases that one or two amino acids deleted from N-terminus of the aminopeptidase coexisted. The processes of the chromatography described above was summarized in table 1.

TABLE 1

Purification process of the aminopepetidase of *Bacillus licheniformis* ATCC 12759

| purification stage | vol. of sample | amino-peptidase (U/ml) | total amino-pepetidase (U/ml) | endo-peptidase (U/ml) |
|---|---|---|---|---|
| culture broth | 6250 | 8.7 | 54000 | 0.43 |
| 2nd TPP | 1520 | 32.95 | 50081 | 0.701 |
| SP-Sepharose | 1650 | 24.95 | 43600 | 0.008 |
| Sephacryl S-200 (conc.) | 35 | 307 | 10700 | 0.023 |
| Mono-S (peak I) | 10.5 | 345 | 3620 | 0.003 |
| Mono-S (peak II) | 6.5 | 243 | 1580 | 0.002 |

TABLE 1-continued

Purification process of the aminopepetidase of *Bacillus licheniformis* ATCC 12759

| purification stage | total endo-peptiase (U/ml) | protein (mg/ml) | specific amino-pepetidase (U/mg) | specific endo-peptidase (U/mg) |
|---|---|---|---|---|
| culture broth | 2365 | 0.94 | 9.26 | 0.46 |
| 2nd TPP | 1065 | 1.07 | 30.79 | 0.66 |
| SP-Sepharose | 14 | 0.07 | 356.4 | 0.11 |
| Sephacryl S-200 (conc.) | 0.8 | 0.25 | 1228 | 0.09 |
| Mono-S (peak I) | 0.032 | 0.232 | 1490 | 0.011 |
| Mono-S (peak II) | 0.013 | 0.149 | 1630 | 0.01 |

Example 9

Structural Peoperties of Aminopeptidase (1) Measurement of Molecular Weight

To determine the molecular weight of aminopeptidase, SDS-PAGE was performed with above sample as shown in FIG. 6. In FIG. 6, lane M is standard protein as molecular weight marker, lane 1 and lane 2 is aminopeptidase of this invention. Molecular weight of the aminopeptidase was identified to be 43–47 kDa approximately.

(2) Amino Acid Sequencing

In order to determine amino acid sequences of N-terminus of aminopeptidase, automated Edman degradation analysis (Geoffrey Zubay, Biochemistry, 2nd Ed., 47–48, 1988) was performed by using amino acid analyzer (Model 471A, Applied Biosynthesis). And phenylthiohydantoin attached amino acid was separated by HPLC column chromatography (220 nm*2.1 mm Model PHT-222, Applied Biosystems, USA) and the retention time was compared. As a result, N-terminal sequence of amino acid was identified to have SEQ. ID. NO: 3 (Lys-Phe-Ser-Lys-Lys-Phe-Asn-Glu-Asn-Arg). And aminopeptidase purified above coexisted with forms in which one and two amino acids were deleted at the N-terminus. These enzymes can be separated by increasing salt concentration of linear gradient in FPLC mono-S-chromatography slowly and had same molecular weights and enzyme activities in the results of SDS-PAGE.

Example 10

Enzymatic Properties of Aminopeptidase (1) Measurement of Optimal pH

Figure 7:
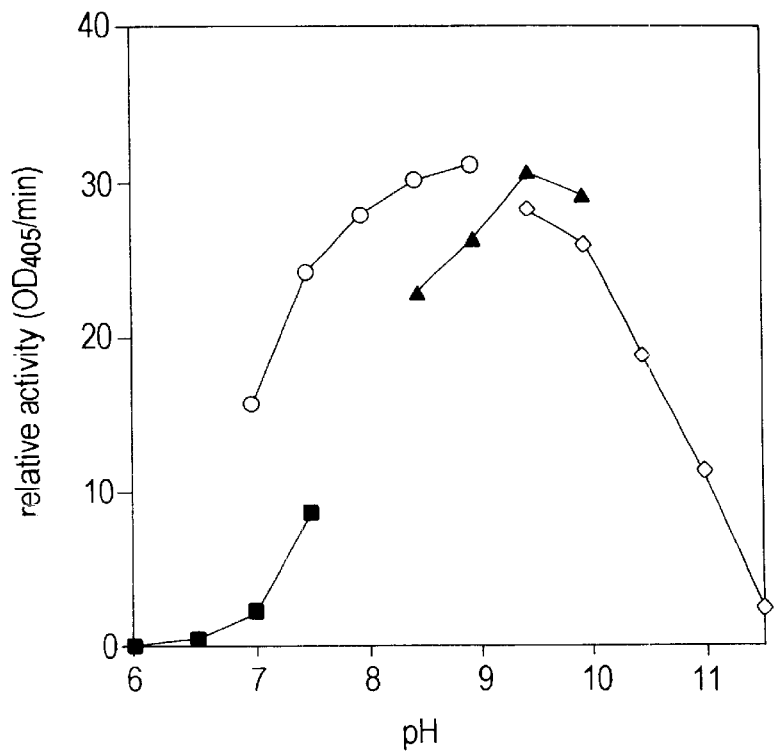
FIG. 7 shows aminopeptidase activities according to pH variation, which are measured by using leucine-p-nitroanilide as substrate.

In order to measure optimal pH range of aminopeptidase, enzyme activities of aminopeptidase were examined at the range of pH6.0–11.5. 0.1M concentration of sodium phosphate (pH 6–7.5), Tris-Cl (pH 7.0–9.0), Boric acid (pH 8.5–10.0), CAPS (3-Cyclohexylamino-1-propanesulfonic acid) buffers were used to control the pH of enzyme reaction. And leucine-p-nitroanilide as synthetic substrate was used to measure the enzyme activities. As a result aminopeptidase of this invention had higher activity at the range of pH 7.5–10.5 and the highest activity at the range of pH 8.5–9.5 as shown in FIG. 7.

(2) Measurement of Optimal Temperature

In order to examine the optimal temperature range, enzyme activities of aminopeptidase were measured at the range of 30–90° C. at every 10° C. interval by using 0.1M of Tris-Cl buffer (pH 8.0) And leucine-p-nitroanilide was used as synthetic substrate. As a result aminopeptidase of this invention had higher activity at the range of 40–70° C. and the highest activity at the range of 50–60° C. as shown in FIG. 7.

(3) Thermostability

In order to examine thermostability of aminopeptidase, purified aminopeptidaes was incubated at 60° C. and 80° C. for 1, 2, 3, 4 and 6 hours respectively, then used to measure the enzyme activities. And the results were compared with that of aminopeptidase which did not treat heat. At that time leucine-p-nitroanilide was used as synthetic substrate.

Figure 9:
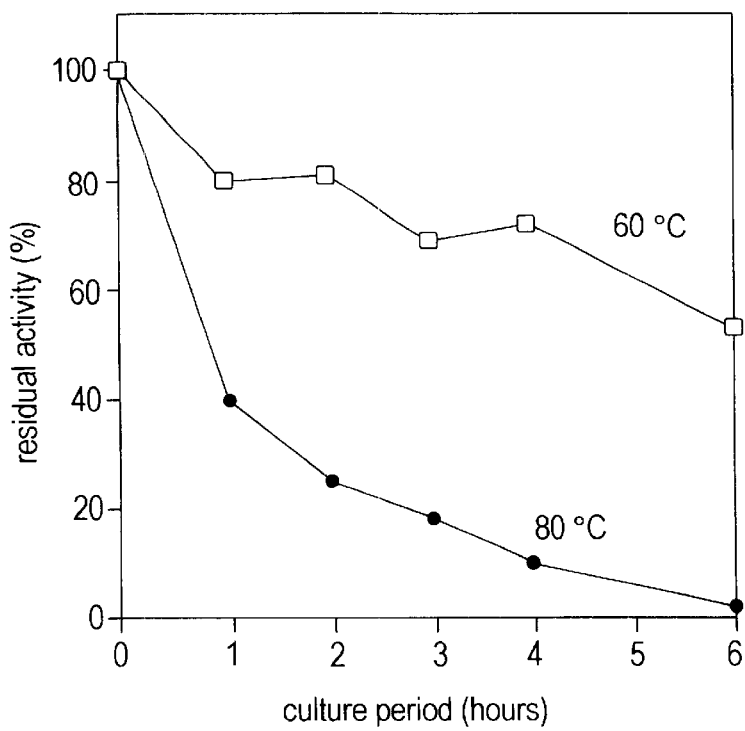
FIG. 9 shows thermostability of aminopeptidase, which is measured by using leucine-p-nitroanilide as substrate.

Since aminopeptidase incubated at 60° C. for 6 hours maintained more than 50% of its activity, the enzyme of this invention is proved to be thermostable as shown in FIG. 9. Thermostability is closely related with stability of protein molecules, so that stable aminopeptidase is not inactivated during purification process and enzyme reaction. Thus enzyme reaction can be performed for long time and the enzyme maintains initial activity continuously. Therefore aminopeptidase of this invention can be utilized very usefully in enzyme reaction requiring long time such as removing a methionine residue from recombinant proteins.

(4) Effect of Chemical Materials

In order to examine chemical materials affecting enzyme activity of aminopeptidase, enzyme activities of aminopeptidase treated for 2 hours with dithiotreitol, iodoacetic acid, ortho-phenanthroline and EDTA as 1, 5 and 20 mMJ respectively were measured. At that time leucine-p-nitroanilide was used as synthetic substrate and the results were shown in table 2.

Precisely aminopeptidase of this invention is identified as metalloprotease since it was inhibited by ortho-phenanthroline more strongly than EDTA. Since the aminopeptidase was inhibited by dithiothreitol reacting with disulfide bond and iodoacetic acid reacting with sulfhydryl group, cysteine residue of the aminopeptidase may perform important role in enzyme reaction.

TABLE 2

Effect of chemical materials affecting enzyme activity

| chemical materials | relative activity (%) | | | |
| --- | --- | --- | --- | --- |
| | 0 mM | 1 mM | 5 mM | 20 mM |
| EDTA | 100 | 93.8 | 83.4 | 66.3 |
| ortho-penanthroline | 100 | 91.9 | 86.8 | 4.7 |
| dithiotreitol | 100 | 0.8 | 0 | 0 |
| iodoacetic acid | 100 | 98.1 | 104.2 | 0 |

Example 11

Substrate Specificity of the Aminopeptidase and Measurement of Chemical Kinetic Constant (1) Preparation of Substrate In order to compare substrate specificity of aminopeptidase of this invention, 2 kinds of substrate were used. In detail, one was synthetic substrates of p-nitroanilide derivative and purchased from Sigma, USA and the other was oligopeptide such as methionyl oligopeptide of SEQ. ID. NO: 1 which have amino acid sequence similar to N-terminus of methionyl HGH and leucyl oligopeptide of SEQ. ID. NO: 2. The oligopeptides of this invention were synthesized.

In order to synthesize oligopeptide mentioned above, solid-phase peptide synthesis was performed automatically in 0.1 mM scale by use of peptide synthesizer (Applied Biosystems 431A, USA). Peptide-resin complex produced in above reaction was cut to obtain oligopeptide prepared as sample by the process of purification and drying. The composition of amino acid in the oligopeptides above was analyzed by amino acid analyzer and amino acid sequence of synthetic peptide was determined exactly by gas chromatography mass analyzer. The oligopeptides were dissolved in DMSO to 30 mM concentration and diluted with DW to 2.5 mM. Then the oligonucleotides diluted was added to reaction mixture at predetermined concentration.

(2) Reaction Condition

Enzyme reaction of aminopeptidase was performed by the process described in Reference Examples. At that time p-nitroanilide derivative was used as synthetic substrate. Leucine p-nitroanilide was used as substrate to perform the reaction in concentration of 0.03125, 0.0625, 0.125, 0.25, 0.5, 1 mM and methionine p-nitroanilide in 0.125, 0.25, 0.5, 1 mM and aminopeptidase in 0.5 U respectively. Above reactions using leucine-p-nitroanilide proceeded for 2 min and methionine-p-nitroanilide for 40 min. Then 70% acetic acid was added to stop the reactions and absorbance at 405 nm was measured. The product concentration was measured by adopting absorbance constant $\epsilon_{405}=9450 M^{-1} cm^{-1}$.

In addition oligopeptide was also used as substrate to perform enzyme reaction by using substrate of known concentration and aminopeptidase in buffer containing 0.1M Tris-Cl, 0.1M NaCl to make 500 $\mu$l reaction volume. The enzyme reaction was performed at 37° C. and after 5 and 10 min 250 $\mu$l of reaction mixture was adopted and added 70% acetic acid to stop the reaction. The reaction mixture was analyzed by performing HPLC chromatography. At that time substrate was used in concentration of 0.125, 0.160, 0.25, 0.75, 1.25 mM regardless of kinds of substrate and aminopeptidase was used in 0.01 U in case of leucyl peptide, 0.2 U in case of methionyl peptide.

(3) Kinetic Parameters of Aminopeptidase

In reaction condition mentioned above, initial velocity of enzyme reaction was measured with varying the substrate concentration. Lineweaver-Burk plot was used to determine Km value and Maximum reaction velocity of aminopeptidase from *Bacillus licheniformis*. In addition kcat and kcat/Km was determined by using Km value and maximum reaction velocity described above. These results were depicted in Table 3 and compared with that of *Aeromonas proteolytica* (*Vibrio prozeolytica*) aminopeptidase (Korean Patent Publication NO. 94-14804) measured by same experiment.

According to general classification method, both the aminopeptidases were classified as leucine aminopeptidase since it reacted with substrate containing N-terminal leucine effectively. Aminopeptidase from *Bacillus licheniformis* had similar kinetic parameters in p-nitroanilide derivative substrate as that of aminopeptidase from *Aeromonas proteolytica*. But in oligopeptide substrate aminopeptidase from *Bacillus licheniformis* had still higher kcat value. Since aminopeptidase from *Bacillus licheniformis* has lower Km value than that from *Aeromonas proteolytica* already reported, it showed higher affinity with substrate. Therefore it was identified that aminopeptidase of the present invention can remove a methionine and leucine residue at N-terminus efficiently.

TABLE 3

Comparison of kinetic parameters of aminopeptidase in various substrate

| aminopeptidase | substrate | Km (mM) | kcat (sec$^{-1}$) | Kcat/Km (mM$^{-1}$sec$^{-1}$) |
|---|---|---|---|---|
| Bacillus licheniformis aminopeptidase | leucine-p-nitroanilide | 0.739 | 130 | 176 |
| | methionine-p-nitroanilide | 1.004 | 2.59 | 2.58 |
| | leucyl oligopeptide | 0.172 ± 0.035 | 275.6 ± 33.9 | 1626 ± 141 |
| | methionyl oligopeptide | 0.387 ± 0.100 | 21.08 ± 3.79 | 56.13 ± 12.35 |
| Aeromonas proteolytica aminopeptidase | leucine-p-nitroanilide | 0.240 | 48 | 200 |
| | methionine-p-nitroanilide | 0.942 | 2.64 | 2.80 |
| | leucyl oligopeptide | 0.336 ± 0.045 | 70.29 ± 4.37 | 211.2 ± 2.4 |
| | methionyl oligopeptide | 0.956 ± 0.680 | 3.23 ± 1.16 | 3.76 ± 1.50 |

Example 12

Preparation of Natural Type HGH (1) Optimization of Reaction Removing N-terminal Methionine from Methionyl HGH In order to prepare natural type HGH by using aminopeptidase from *Bacillus licheniformis*, optimal condition of reaction removing N-terminal methionine of protein was examined as described below. In principle reaction mixture containing 1 mg/ml methionyl HGH (final 0.1 mg), 50 mM Tris-Cl (pH 8.0), 0.1M NaCl, 1 mM PMSF was prepared and 0.5 U of aminopeptidase was added to make 100 μl of final volume. Then the reaction was performed at 37° C. for 30 min and 11 μg of 100% TCA was added to stop the reaction. The reaction mixture was centrifuged to precipitate proteins by small-scale centrifuge at 14000 rpm for 5 min. The precipitate of protein was washed twice with acetone and was dried. Automatic Edman degradation was performed by amino acid sequence analyzer (Model 471A, Applied Biosystems, USA) with dried sample.

In order to examine removal rate of methionine residue, methionine versus phenylalanine ratio detected at 1st cycle was measured. In order to examine optimal pH of above reaction, the removal rate of methionine from methionyl HGH was measured in pH range of 7.0–11.5. As buffer solution, Tris-Cl (pH 7.0–9.0), boric acid (pH8.5–10.0) and CAPS (pH9.5–11.5) was used in 50 mM to regulate pH in above reaction.

Figure 10:
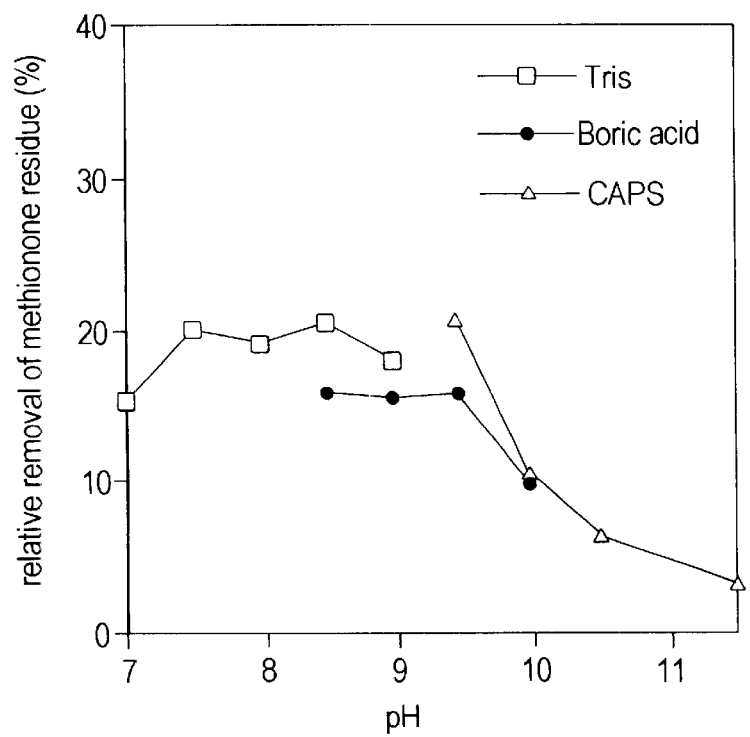
FIG. 10 shows patterns removing methionine according to pH variation for preparing natural type HGH from methionyl HGH.
Figure 11:
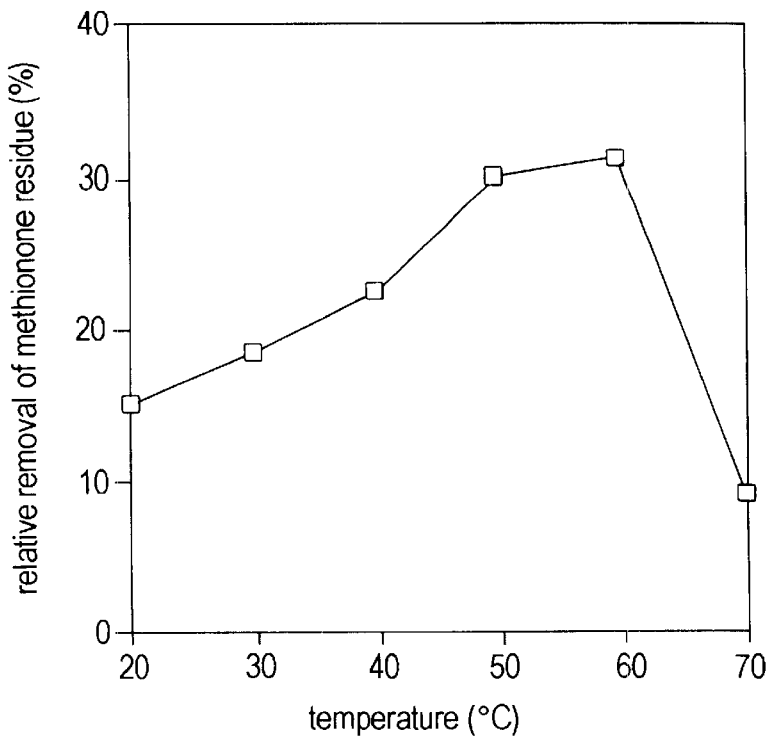
FIG. 11 shows patterns removing methionine according to temperature variation for preparing natural type HGH from methionyl HGH.
Figure 12:
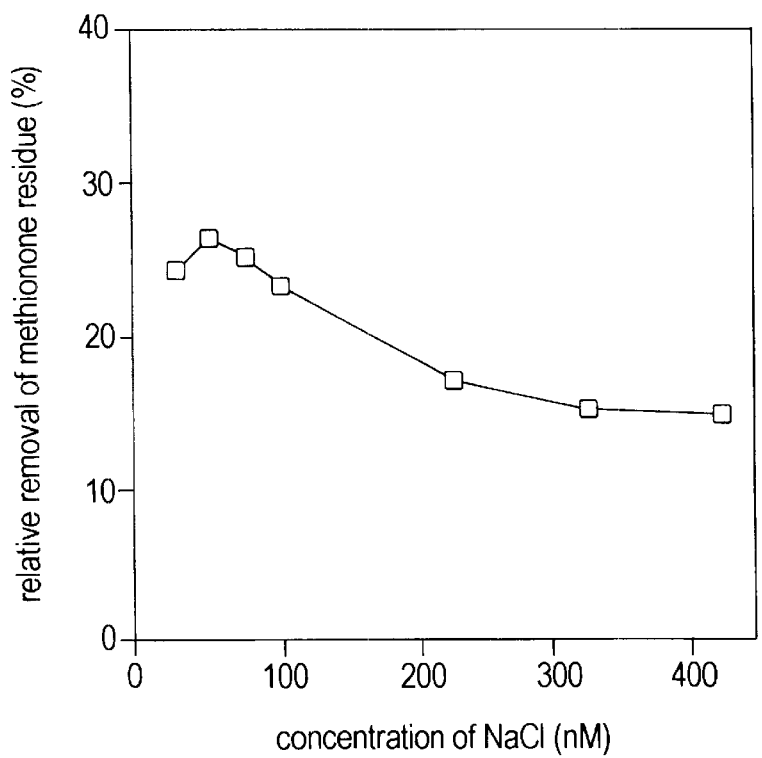
FIG. 12 shows patterns removing methionine according to NaCl concentration variation for preparing natural type HGH from methionyl HGH.

As a result, optimal pH range which can be used to prepare natural type HGH by using aminopeptidase is 7.5–9.5 as shown in FIG. 10. In order to examine optimal temperature, the removal rate of methionine residue at N-terminus was measured at the range of 20–70° C. and the results are shown in FIG. 11. Optimal temperature range removing methionine was 50–60° C. But at high temperature removal rate of methionine became low due to precipitation of HGH. Considering stability of HGH, low temperature below 37° C. is more preferable than high temperature of 50–60° C. As shown in FIG. 12, NaCl can be added to 430 mM in reaction mixture, preferably about 100 mM.

(2) Preparation of Natural Type HGH

Figure 13:
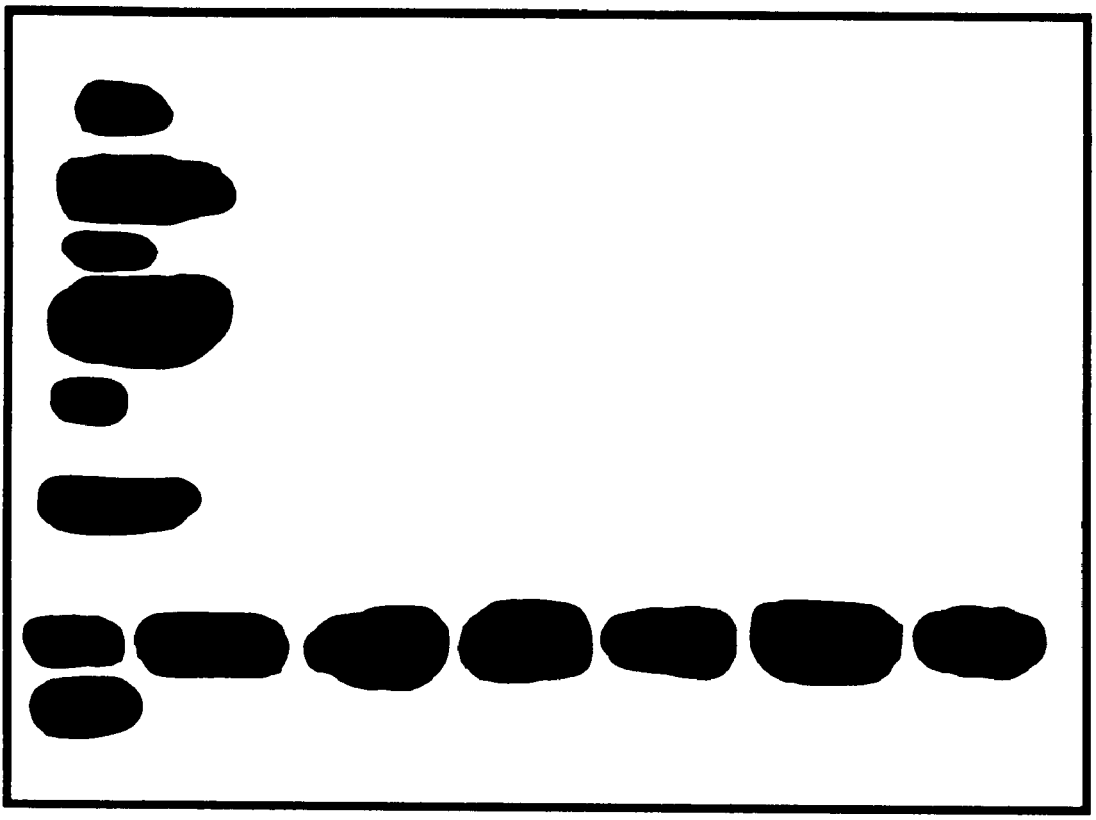
FIG. 13 shows natural type HGH which is prepared from methionyl HGH by the process performing Mono-Q chromatography and SDS-PAGE.

About 1 mg of methionyl HGH and reaction buffer (50 mM Tris-Cl, pH 8.0, 100 mM NaCl, 1 mM PMSF) containing 10 U of aminopeptidase were mixed (final volume 1 ml) in dialysis tube and reacted at 37° C. for 24 hours in water bath dialyzing with same buffer. After 24 hours the above reaction mixture was dialyzed again with Tris-Cl (pH 8.0) at 4° C. sufficiently to complete the reaction. Then Mono-Q ion exchange chromatography (HPLC chromatography) was performed to elute HGH with 20 mM Tris-Cl containing 0.1M NaCl. At that time HGH recovered above was absolutely pure without aminopeptidase and other contaminants and the results were identified by SDS-PAGE as shown in FIG. 13.

Figure 14:
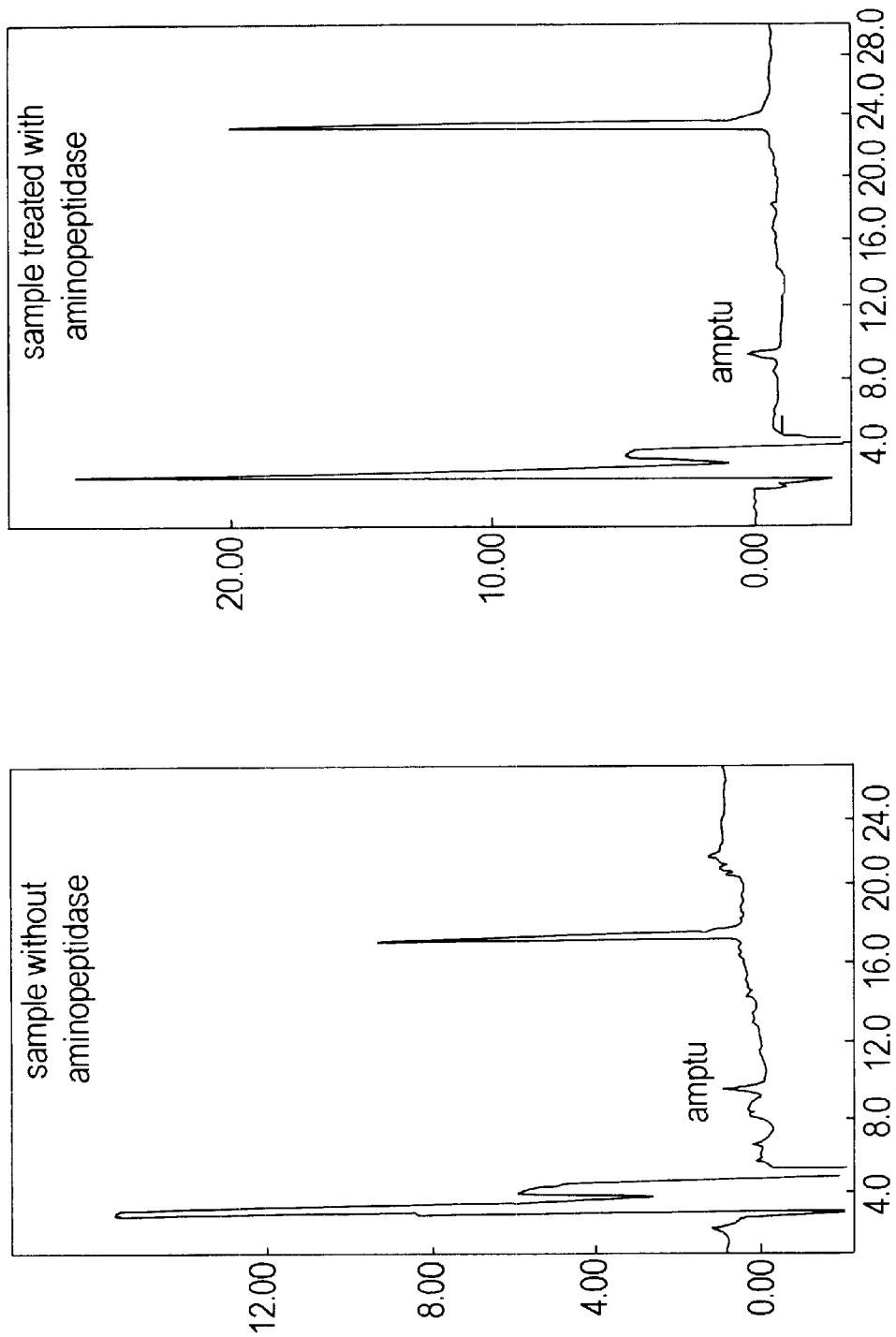
FIG. 14 shows results analyzing amino acid sequence of natural type HGH prepared by the above process.

And amino acids at N-terminus gf HGH recovered above was analyzed by amino acid sequence analyzer (model 471A, Applied Biosystems, USA) as shown in FIG. 14. As a result, it was identified that aminopeptedase of the present invention remove N-terminal methionine of methionyl HGH completely and replace N-terminus methionine with phenylalanine to produce new natural type HGH.

Figure 15:
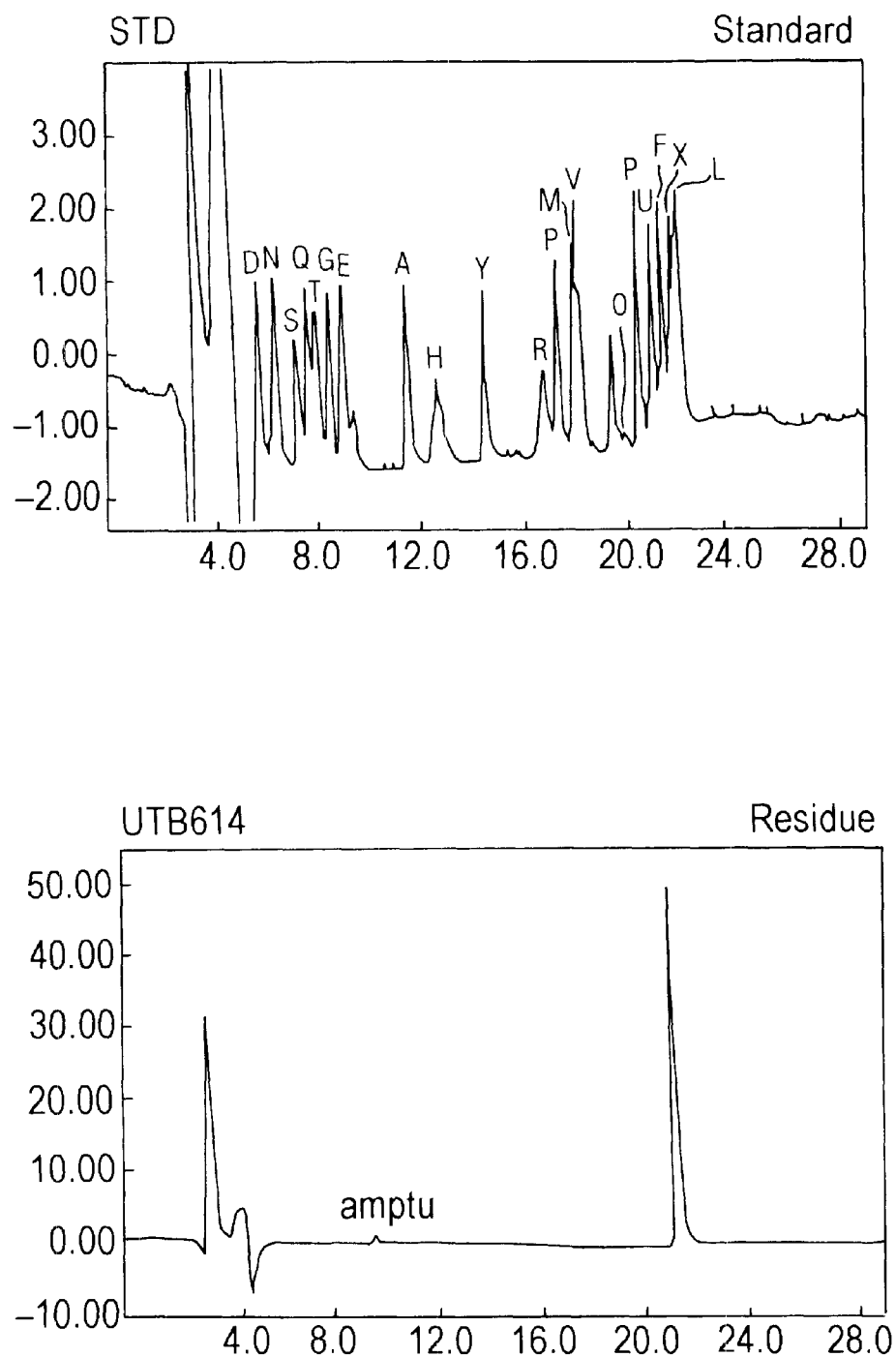
FIG. 15 shows results analyzing amino acid sequence of natural type HGH prepared by the above process.

(3) Preparation of Natural Type HGH in Large Scale 50 mg of amonopeptidase was treated in 50 mg of methionyl HGH at 37° C. for 24 hours in a condition mentioned above. HGH was obtained by the process wherein the sample was treated with aminopeptidase, diafiltrated to reduce the salt concentration, proceeded to ion exchange chromatography using DEAE-sepharose (Pharmacia) and recovered. N-terminal amino acid sequence of HGH recovered was determined by amino acid sequence analyzer as shown in FIG. 15. As a result, it was identified that HGH produced by the above process had phenylalanine at the N-terminus due to methionine removal.

Example 13

Purification of Aminopeptidase from *Bacillus licheniformis* KCTC 3058 (ATCC 11946)

*Bacillus licheniformis* KCTC 3058 was cultured by the same process described in Example 7. Culture broth (approximately 8 L) was centrifuged at 8000 rpm for 20 min. The resulting supernatant was recovered, and concentrated into about 1.6 L by using concentrator (Amicon Spiral Cartridge, MWCO 10000). Into above concentrating solution 10% of acetic acid was added to adjust pH 5.0 and ammonium sulfate was added to make 40% of final concentration (saturation concentration). And the same volume of ter-butanol was added, mixed for 1 hour, then centrifuged at 8000 rpm for lawn to recover lower aqueous layer by using separating funnel (1 st TTP). Then pH was adjusted to 6.0 by adding 0.5N NaOH and ammonium sulfate was also added to make 85% solution of final concentration (saturation concentration). Then the same volume of ter-butanol was added, mixed for 1 hour, then centrifuged at 8000 rpm for 10 min to recover protein precipitation layer in middle layer (2nd TTP).

Precipitated protein was dissolved in 20 mM PBS (pH 6.8) and centrifuged at 10,000 rpm for 20 min to remove contamination precipitate. Considering conductivity of the solution, salt concentration was diluted with same buffer below 0.3M approximately. Then 500 ml of SP-Sepharose (Pharmacia) column was prepared and equilibrated with the same buffer. The above protein sample was injected, then the column was washed with PBS buffer containing 0.3–0.4M NaCl (flow rate 15 ml/min). Aminopeptidase was eluted with linear concentration gradient of 0.3–0.4M NaCl to 1M NaCl (flow rate 10 ml/min).

Each fraction eluted from SP-Sepharose column was examined to measure enzyme activity of aminopeptidase. And fractions showing the enzyme activity were collected and concentrated into 20 ml by ultrafiltration (Amicon stirred cell type). Then gel filtration chromatography was performed to purify the aminopeptidase of this invention.

The purification process described above was performed by two different buffer systems. At first process, 20 mM Tris-Cl buffer (pH 7.5) containing 0.5 M NaCl and at second process 20 mM PBS buffer (pH 6.8) containing 0.5 M NaCl, 0.1% tween 20 were utilized to perform gel permeation chromatography. The processes of the chromatography described above was summarized in table 4 and table 5.

Above fractions obtained by using gel filtration chromatography was concentrated and diluted. Then the diluted sample was absorbed into FPLC mono-S column (0.5 cm*5 cm) and proteins were eluted with linear concentration gradient of 0.4–1M NaCl for obtaining pure aminopeptidase.

TABLE 4

Purification process of the aminopeptidase of Bacillus licheniformis KCTC 3058 in which 20 mM Tris-Cl (pH 7.5) was used in gel filtration.

| purifiaion stage | vol. of sample | protein conc. (mg/ml), [total mmg] | aminopeptidase activity | | |
|---|---|---|---|---|---|
| | | | U/ml | U/mg | total (U) |
| culture broth | 10,280 | 12,181 [125,000] | 13.67 | 1.12 | 140,528 |
| conc. spt. | 2,750 | 3.174 [8,700] | 31.22 | 9.87 | 82,855 |
| 2nd TTP | 1,000 | 1.664 [1,644] | 69.9 | 42.5 | 69,900 |
| SP-Sepharose | 18 | 1.773 [31.9] | 1401 | 790.7 | 25,222 |
| S-200 | 24.5 | 0.394 [9.65] | 442 | 1,122 | 10,829 |

| purifiaion stage | vol. of sample | protein conc. (mg/ml), [total mmg] | endopeptidase activity | | |
|---|---|---|---|---|---|
| | | | U/ml | U/mg | total (U) |
| culture broth | 10,280 | 12,181 [125,000] | 0.710 | 0.058 | 7,299 |
| conc. spt. | 2,750 | 3,174 [8,700] | 0.778 | 0.246 | 2,140 |
| 2nd TTP | 1,000 | 1.664 [1,644] | 0.708 | 0.431 | 708 |
| SP-Sepharose | 18 | 1.773 (31.9) | 0.056 | 0.032 | 1.01 |
| S-200 | 24.5 | 0.394 [9.65] | 0.031 | 0.079 | 0.76 |

TABLE 5

Purification process of the aminopeptidase of Bacillus licheniformis KCTC 3058 in which 20 mM PBS (pH 6.8) buffer containing 0.5 M NaCl and 0.1% Tween 20 was used in gel filtration.

| purification stage | vol. of sample | protein conc. (mg/ml), [total mmg] | aminopeptidase activity | | |
|---|---|---|---|---|---|
| | | | U/ml | U/mg | total (U) |
| culture broth | 8,100 | 14.216 [115,000] | 12.49 | 0.88 | 101,169 |
| conc. spt. | 16,000 | 11.214 [17,900] | 83.63 | 7.48 | 133,813 |
| 2nd TTP | 1,000 | 2.132 [2,132] | 111.18 | 52.1 | 111,177 |
| SP-Sepharose | 32 | 2.753 [88.1] | 3.639 | 1,321 | 116,362 |
| S-200 | 12.2 | 1.765 [21.5] | 1,520 | 862.5 | 18,544 |
| S-200 | 13.3 | 1.715 [22.8] | 1,824 | 1,064 | 24,259 |
| S-200 | 11 | 0.317 [3.49] | 648 | 2,042 | 7,128 |
| S-200 | 12.4 | 0.468 [5.8] | 834 | 1,783 | 10,342 |
| S-200 | 11.5 | 0.879 [10.1] | 1,660 | 1,890 | 19,090 |

| purifiaion stage | vol. of sample | protein conc. (mg/ml), [total mmg] | endopeptidase activity | | |
|---|---|---|---|---|---|
| | | | U/ml | U/mg | total (U) |
| culture broth | 8,100 | 14.216 [115,000] | 0.266 | 0.019 | 2,155 |
| conc. spt. | 16,000 | 11.214 [17,900] | 0.507 | 0.045 | 811 |
| 2nd TTP | 1,000 | 2.132 [2,132] | 0.612 | 0.287 | 612 |
| SP-Sepharose | 32 | 2.753 [88.1] | 0.047 | 0.017 | 1.50 |
| S-200 | 12.2 | 1.765 [21.5] | 0.011 | 0.006 | 0.134 |
| S-200 | 13.3 | 1.715 [22.8] | 0.010 | 0.006 | 0.133 |
| S-200 | 11 | 0.317 [3.49] | 0.023 | 0.072 | 0.253 |
| S-200 | 12.4 | 0.468 [5.8] | 0.024 | 0.051 | 0.298 |
| S-200 | 11.5 | 0.879 [10.1] | 0.046 | 0.052 | 0.529 |

Example 14

Structural Characteristics of Aminopeptidase from Bacillus licheniformis KCTC 3058

(1) Measurement of Molecular Weight

Figure 16A:
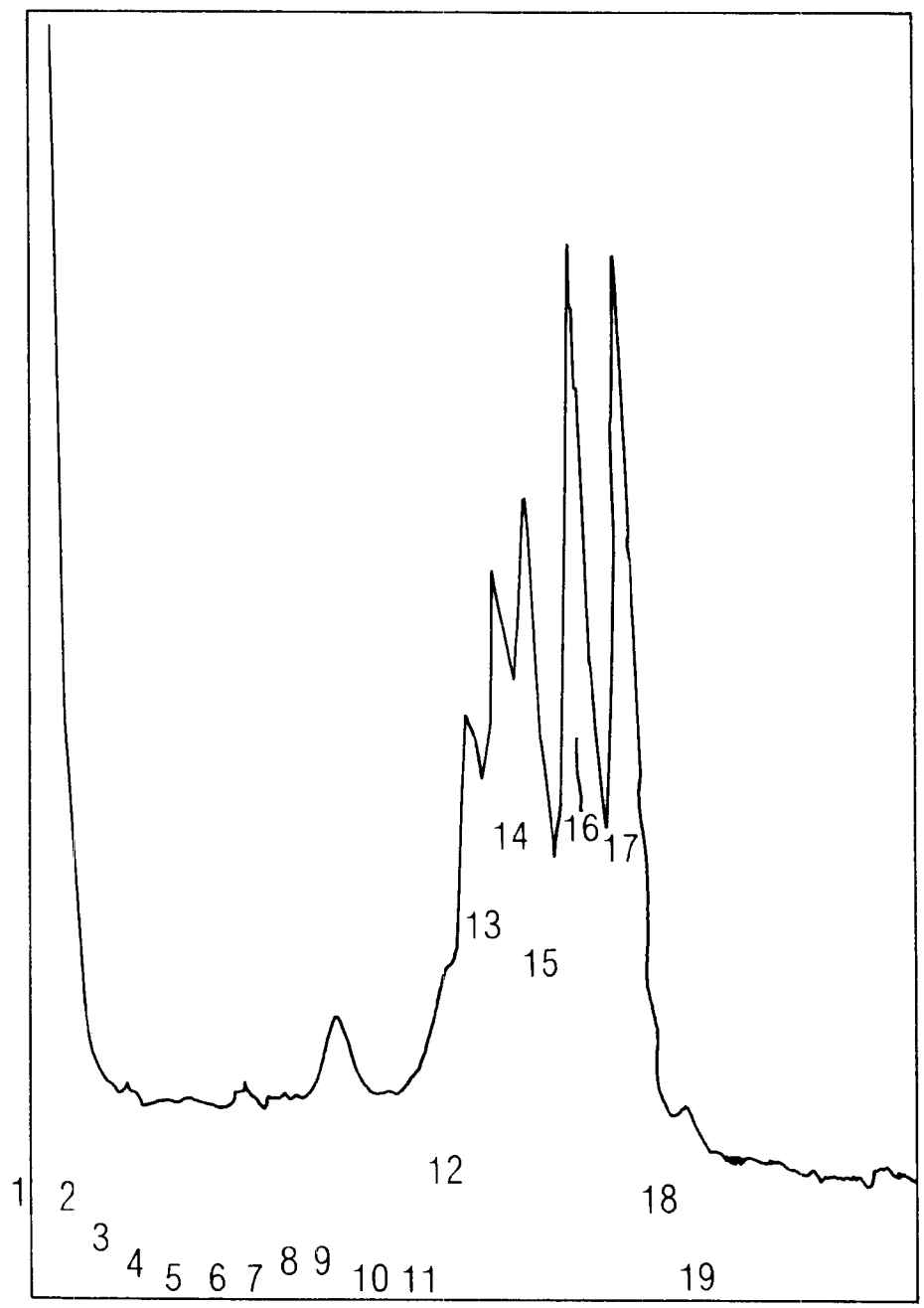
FIG. 16a shows the chromatogram of aminopeptidase which is purified from *Bacillus licheniformis* by the process performing Mono-S chromatography.
Figure 16B:
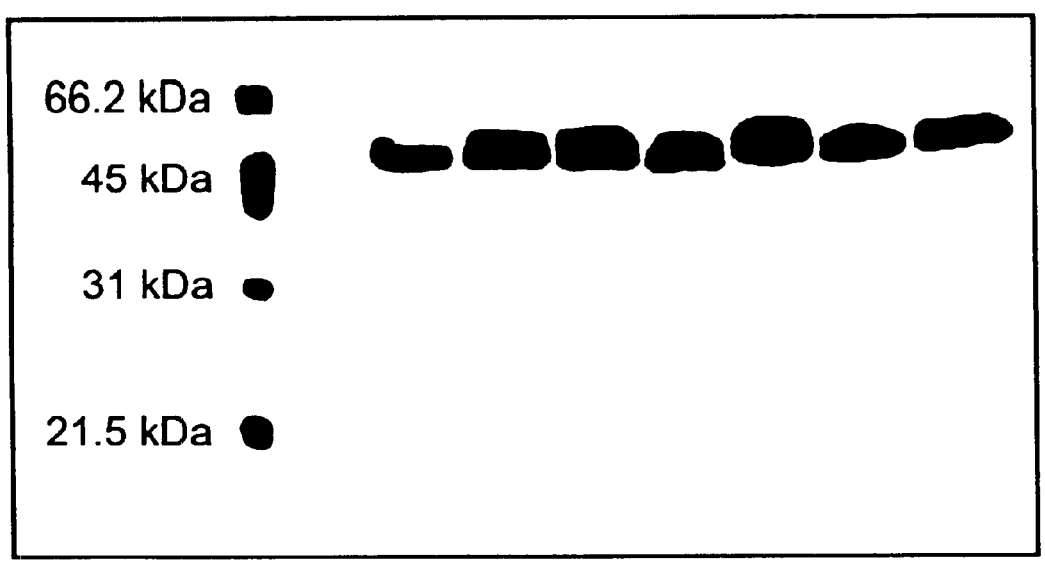
FIG. 16b shows aminopeptidase which is purified from *Bacillus licheniformis* by the process performing Mono-S chromatography and SDS-PAGE.

To determine the molecular weight of aminopeptidase, which was purified from Bacillus licheniformis KCTC 3058 (ATCC 11946) in Example 13, the fractions resolved on FPLC Mono-S column chromatography were analyzed in SDS-PAGE. As a result, all peaks of the aminopeptidase which showed different elution time was identified to have the same molecular weights in spite of the above chromatogram as shown in FIG. 16a and FIG. 16b. And aminopeptidase derived from Bacillus licheniformis KCTC 3058 also has the same molecular weights with that of aminopeptidase from Bacillus licheniformis ATCC 12759. Molecular weight of the aminopeptidase was identified to be 43–47 kDa approximately.

(2) Amino Acid Sequencing

In order to determine amino acid sequence of the N-terminus of aminopeptidase derived from Bacillus licheniformis KCTC 3058 (ATCC 11946), automated Edman degradation analysis (Geoffrey Zubay, Biochemistry, 2nd Ed., 47–48, 1988) was performed by using amino acid analyzer of Example 9. As a result, the N-terminal sequence of amino acid was identified to have SEQ. ID. NO: 4 (Lys-Phe-Ser-Lys-Lys-Phe-Asn-Glu-Asn-Arg-Ala-Tyr-Gln-Thr-Ile-Tyr-His-Leu). And the aminopeptidase purified above coexisted with forms in which the N-terminal lysine was deleted at the N-terminus and 9th asparagine was substituted for aspartic acid. The amino acid sequence identified above was exactly same with that of aminopeptidase derived from *Bacillus licheniformis* ATCC 12759.

Summarizing the results described above, the aminopeptidases derived from different strains of *Bacillus licheniformis* are same, since aminopeptidases derived from *Bacillus licheniformis* KCTC 3058 and ATCC 12759 respectively has the same molecular weight and amino acid sequence at the N-terminal.

The aminopeptidases of the present invention is useful since they are purified from *Bacillus licheniformis* and remove the N-terminal methionine residue specifically. Since aminopeptidases recognize Met-X-Pro sequence at the N-terminus, in addition to HGH all the proteins having X-Pro-sequence at the N-terminus could be changed easily to natural type proteins having complete activity after mass production in bacterial cell. And the aminopeptidases of the present invention are also proper to be used in the reaction mentioned above due to their thermostability.

What is claimed is:

1. An aminopeptidase isolated from *Bacillus licheniformis* capable of cleaving an amino-terminal methionine from peptides or proteins, comprising the amino-terminal amino acid sequence set forth in SEQ ID NO: 3, and having a molecular weight within the range of 43 kDa to 47 kDa.

2. The aminopeptidase according to claim 1, wherein the amino-terminal amino acid sequence of the peptides or proteins is Met-X-Pro sequence, wherein said X indicates any amino acid available.

3. The aminopeptidase according to claim 2, wherein the X is phenylalanine.

4. A process for preparing the aminopeptidase of claim 1 which comprises culturing *Bacillus licheniformis* strains capable of producing said aminopeptidase, centrifuging the culture broth, concentrating the resulting supernatant, and purifying the aminopeptidase from the supernatant.

5. The process according to claim 4, wherein the *Bacillus licheniformis* strains are selected from group consisting of ATCC 12759, KCTC 3058, KCTC 3045 and KCTC 1030.

6. A method for preparing a peptide or protein having a native amino-terminus lacking a methionine amino-acid which comprises contacting a recombinantly expressed peptide or protein with the aminopeptidase of claim 1 under conditions permitting cleavage of the methionine with the aminopeptidase and purifying the cleavage product.

7. The method according to claim 6, wherein the amino-terminal amino acid sequence of the recombinant protein is Met-X-Pro sequence wherein said X indicates any amino acid available.

8. The method according to claim 7, wherein the recombinant expressed protein is methionyl human growth hormone (HGH).

9. The method according to claim 8, wherein the contacting is at a pH from 7.0 to 9.5, at a temperature from 20° C. to 60° C. and at a concentration of NaCl from 30 mM to 230 mM.

10. The method according to claim 8, wherein the aminopeptidase is used in 0.2–20 U per 1 mg of methionyl HGH.

11. The method according to claim 8, wherein after contacting the methionyl HGH with the aminopeptidase, HGH having a native amino-terminus lacking a methionine amino-acid is purified by performing ion exchange resin chromatography.

* * * * *

```
                         SEQUENCE LISTING (1) GENERAL INFORMATION:

(iii) NUMBER OF SEQUENCES: 4

(2) INFORMATION FOR SEQ ID NO: 1 :

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 1

Met Phe Pro Thr Glu Pro Ser
1               5

(2) INFORMATION FOR SEQ ID NO: 2 :

(i) SEQUENCE CHARACTERISTICS:
         (A) LENGTH: 7 anino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 2

Leu Phe Pro Thr Glu Pro Ser
1               5

(2) INFORMATION FOR SEQ ID NO: 3 :

(i) SEQUNCE CHARACTERISTICS :
         (A) LENGTH: 10 amino acids
         (B) TYPE: amino acid
         (C) STRANDEDNESS: single
         (D) TOPOLOGY: linear (ii) MOLECULE TYPE: N-terminal amino acids (xi) SEQUENCE DESCRIPTION: SEQ ID NO: 3

Lys Phe Ser Lys Lys Phe Asn Glu Asn Arg
1               5                   10

(2) INFORMATION FOR SEQ ID NO: 4 :

(i) SEQUENCE CHARACTERISTICS:
         (A) LENGTH: 18 amino acids
         (B) TYPE: amino acid
         (C) STRANDEDNESS: single
         (D) TOPOLOGY: linear
```

-continued

```
    (ii) MOLECULE TYPE: N-terminal amino acids (xi) SEQUENCE DESCRIPTION: SEQ ID NO: 4

Lys Phe Ser Lys Lys Phe Asn Glu Asn Arg Ala Tyr Gln Thr Ile
 1               5                  10                  15

His Leu
```